United States Patent

Nogawa et al.

[11] Patent Number: 5,931,646
[45] Date of Patent: Aug. 3, 1999

[54] BLOOD DELIVERY INSTRUMENT FOR REGULATING THE AMOUNT OF BLOOD STORED IN AN ACCUMULATOR INDEPENDENT OF THE PUMPING OPERATION

[75] Inventors: Atsuhiko Nogawa; Yukitoshi Katou; Mitsuaki Ogihara, all of Nakai-Machi, Japan

[73] Assignee: Terumo Kabushiki Kaisha, Tokyo, Japan

[21] Appl. No.: 08/725,228

[22] Filed: Oct. 3, 1996

[30] Foreign Application Priority Data

Oct. 3, 1995 [JP] Japan ................................ 7-282474

[51] Int. Cl.[6] .................................................. F04B 45/10
[52] U.S. Cl. .............................................. 417/395; 417/384
[58] Field of Search ..................... 604/4, 38, 141, 604/320, 408, 321, 405, 317; 23/258.5; 422/45; 210/195.2, 188, 806, 97; 128/214 R, 276; 55/16; 417/395, 411, 384, 386, 387, 389

[56] References Cited

U.S. PATENT DOCUMENTS

| | | | |
|---|---|---|---|
| 3,907,504 | 9/1975 | Hammond et al. | 23/258.5 |
| 4,599,093 | 7/1986 | Steg, Jr. | 55/16 |
| 4,610,656 | 9/1986 | Mortensen | 604/4 |
| 5,486,099 | 1/1996 | Montoya | 138/119 |
| 5,512,042 | 4/1996 | Montoya et al. | 604/403 |

FOREIGN PATENT DOCUMENTS

| | | |
|---|---|---|
| 0 030 760 | 6/1981 | European Pat. Off. . |
| 0 111 918 | 6/1984 | European Pat. Off. . |
| 0 309 642 | 4/1989 | European Pat. Off. . |
| 93/01858 | 2/1993 | WIPO . |

*Primary Examiner*—Charles G. Freay
*Assistant Examiner*—Robert Z. Evora
*Attorney, Agent, or Firm*—Burns, Doane, Swecker & Mathis, LLP

[57] ABSTRACT

A blood reservoir includes a blood tank, a blood accumulator connected in fluid communication with an outlet of the tank for receiving blood from the tank, and a pumping device for driving the accumulator to displace blood out of the accumulator. The accumulator typically in the form of a flexible bag is adapted to store blood in an amount proportional to the volume of blood in the tank when the volume of blood in the tank is reduced below a predetermined value. The pumping device is operated for intermittent blood delivery and can regulate the amount of blood displaced out of the accumulator.

29 Claims, 29 Drawing Sheets

F I G. 25
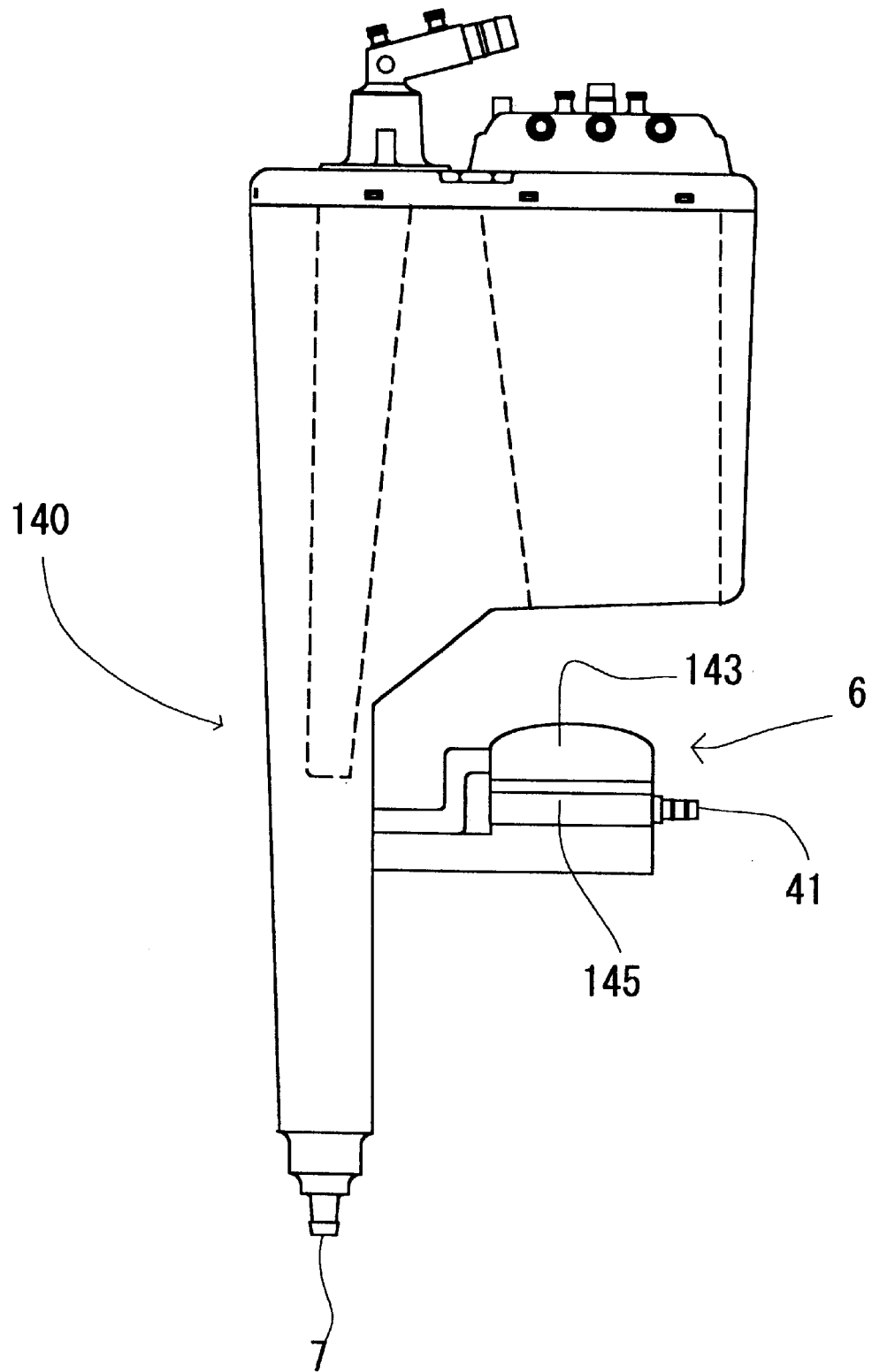

F I G. 32
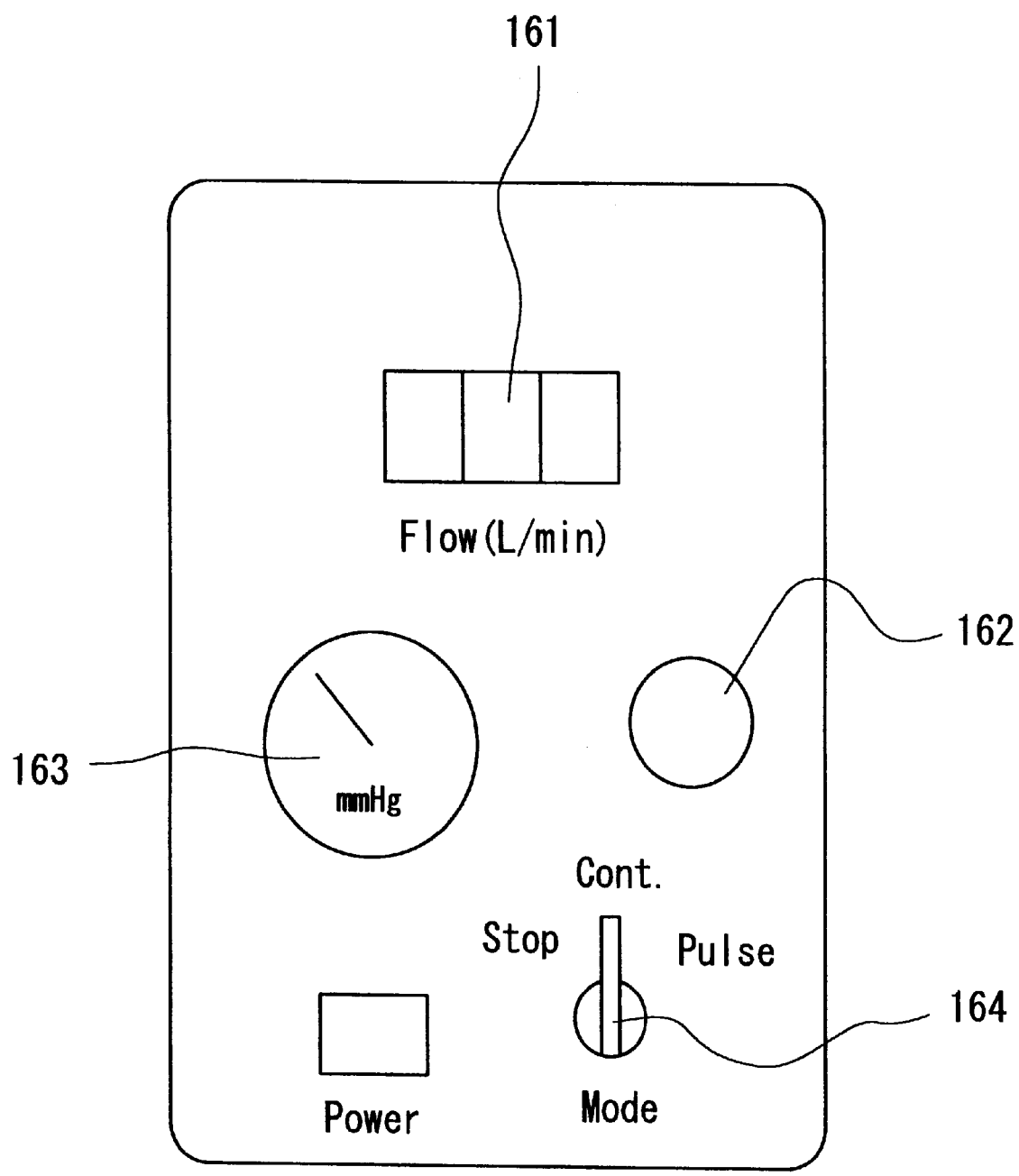

BLOOD DELIVERY INSTRUMENT FOR REGULATING THE AMOUNT OF BLOOD STORED IN AN ACCUMULATOR INDEPENDENT OF THE PUMPING OPERATION

BACKGROUND OF THE INVENTION

1. Field of the Invention

This invention relates to a blood reservoir for use in an extracorporeal blood circulation circuit with an artificial lung, the reservoir having a blood accumulating/delivering means for temporarily storing blood and delivering the once stored blood. It also relates to a blood delivery instrument and blood delivery apparatus for use in an extracorporeal blood circulation circuit including a blood tank, the instrument and apparatus being disposed downstream of the tank for delivering blood to a downstream destation.

2. Prior Art

Heart surgery often uses an extracorporeal blood circulation circuit having incorporated therein an artificial lung for removing carbon dioxide from blood and adding oxygen to blood instead of the living lung. The extracorporeal circulation circuit is to drain blood from the patient's vein, subject the blood to gas exchange in the artificial lung, and return the blood to the patient's artery. The extracorporeal circulation circuit also includes a cardiotomy line for sucking in blood from the operation area, removing foreign matter therefrom, and returning the blood.

In general, the exacorporead circulation circuit with an artificial lung includes a blood tank for temporarily storing blood drained from the patient and a cardiotomy reservoir for filtering blood sucked from the operation area and temporarily storing the blood. The blood tank and cardiotomy reservoir serve a buffering function of adjusting the amount of blood in the circuit and maintaining a constant amount of blood returned to the patient.

There is a situation that the volume of blood in the blood tank becomes zero during extracorporeal blood circulation. If the blood feed pump continues to operate, air can be fed into the extracorporeal circulation circuit. To avoid such inconvenience, the tank is provided with a level sensor for monitoring the volume of blood in the tank. When the sensor detects that the volume of blood in the tank is below a predetermined value, the feed pump is interrupted to stop blood delivery action until the volume of blood in the blood tank is restored. The temporary interruption of blood delivery, however, is undesirable because it causes blood stagnation throughout the circuit including the artificial lung.

Therefore, an object of the present invention is to provide a blood reservoir, blood delivery instrument and blood delivery apparatus which can regulate the amount of blood delivered in accordance with the volume of blood in the blood tank when the volume of blood in the blood tank is reduced below a predetermined value.

SUMMARY OF THE INVENTION

In a first aspect, the present invention provides a blood reservoir comprising a blood tank having a blood outlet and a blood accumulator connected in fluid communication with the tank outlet for receiving blood from said tank and adapted to store blood in an amount proportional to the volume of blood in said tank when the volume of blood in said tank is reduced below a predetermined value, a pumping means adapted to be intermittently operated for driving said accumulator to displace blood out of said accumulator for blood delivery purpose, said pumping means being able to regulate the amount of blood displaced out of said accumulator.

In a second aspect, the present invention provides a blood reservoir comprising a blood tank having a blood outlet, a blood accumulator connected in fluid communication with the tank outlet for receiving blood from said tank and adapted to store blood in an amount proportional to the volume of blood in said tank when the volume of blood in said tank is reduced below a predetermined value, a first check valve disposed between said tank and said accumulator for restraining blood passage to the tank side, a second check valve disposed downstream of said accumulator for restraining blood passage from a side downstream of said accumulator, and a pumping means for driving said accumulator for delivering blood out of said accumulator.

In a third aspect, the present invention provides a blood reservoir comprising a blood tank having a blood outlet, a blood accumulator connected in fluid communication with the tank outlet for receiving blood from said tank and adapted to store blood in an amount proportional to the volume of blood in said tank when the volume of blood in said tank is reduced below a predetermined value, and a containment having said accumulator received therein, said containment being provided with a port to be coupled to hydraulic or pneumatic means for pressurizing the interior of said containment.

In a fourth aspect, the present invention provides a blood delivery instrument for use in an extracorporeal blood circulation circuit including a blood tank, comprising a coupling connected to said tank, a blood accumulator connected to said coupling for receiving blood from said tank and adapted to store blood in an amount proportional to the volume of blood in said tank when the volume of blood in said tank is reduced below a predetermined value, a pumping means adapted to be intermittently operated for driving said accumulator to deliver blood from said accumulator to a destination, a first check valve disposed between said tank and said accumulator for restraining blood passage to the tank side, and a second check valve disposed downstream of said accumulator for restraining blood passage from a side downstream of said accumulator.

In a fifth aspect, the present invention provides a blood delivery apparatus for use in an extracorporeal blood circulation circuit including a blood tank, comprising a means for regulating the amount of blood delivered so as to be proportional to the volume of blood in said tank when the volume of blood in said tank is reduced below a predetermined value.

In a sixth aspect, the present invention provides a blood delivery apparatus for use in an extracorporeal blood circulation circuit, comprising a blood tank, a sensor means for detecting the varying volume of blood in said tank to produce a varying signal, a blood feed pump for delivering blood, and a means for regulating the amount of blood delivered so as to be proportional to the volume of blood in said tank when the volume of blood in said tank is reduced below a predetermined value.

BRIEF DESCRIPTION OF THE DRAWINGS

These and further features of the present invention will be apparent with reference to the following description and drawings, wherein:

FIG. 17 is a front elevational view of the reservoir.

FIG. 18 is a left side view of the reservoir.

FIG. 19 is a top view of the reservoir.

FIG. 20 is a cross section taken alone lines XX—XX of FIG. 17.

FIG. 21 is a cross section taken along lines XXI—XXI of FIG. 17.

FIG. 22 is a partial cross-sectional view of FIG. 17.

FIG. 23 is a schematic view for explaining the operation of the blood reservoir of FIG. 17.

FIGS. 25 to 27 show a blood reservoir according to a still further embodiment of the invention.

FIG. 25 is a front elevation of the reservoir.

FIG. 26 is a side view of the reservoir.

FIG. 27 is a partial cross-sectional view of the reservoir of FIG. 25.

FIG. 28 is a front elevation of the reservoir.

FIG. 29 is a side view of the reservoir of FIG. 28.

FIG. 30 is a partial cross-sectional view of the reservoir of FIG. 28.

FIG. 31 is a partial cross-sectional view of the reservoir of FIG. 28.

FIG. 32 is a schematic view explaining a fluid feed unut for use in combination with the blood reservoir according to the invention.

DESCRIPTION OF THE PREFERRED EMBODIMENTS

Figure 1:
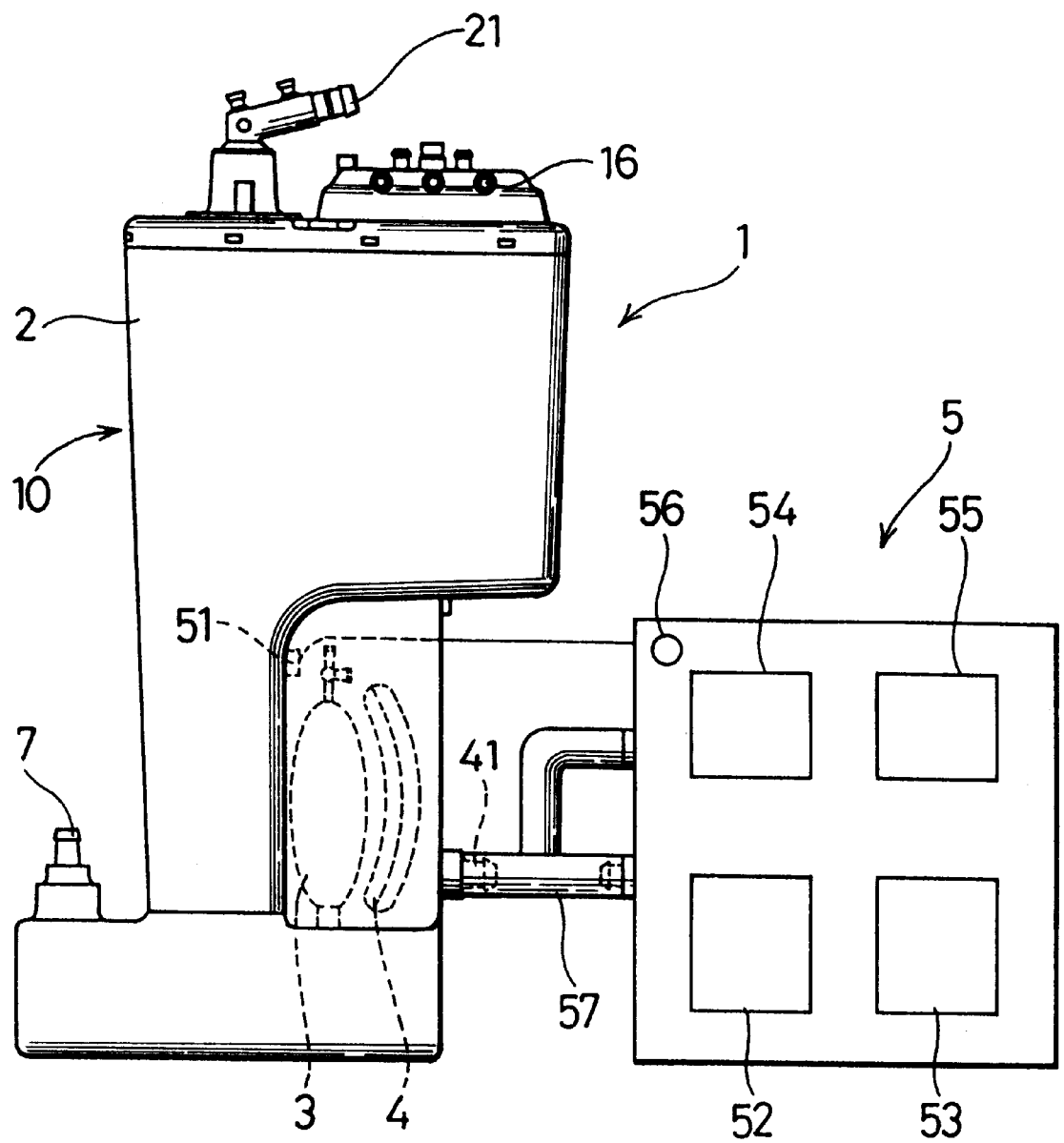
FIG. 1 is a schematic view of a blood delivery apparatus comprising a blood reservoir and a fluid feed unit according to a first embodiment of the invention.

The blood reservoir and blood delivery apparatus according to the invention are described in detail in conjunction with several preferred embodiments shown in the drawings.

Referring to FIGS. 1 through 9, a blood delivery apparatus 1 according to the invention includes a blood reservoir 10 and a blood delivery fluid feed unit 5.

The blood reservoir 10 includes a blood tank 2 having blood inlets 21, 22 and a blood outlet 26, a blood accumulator 3 in communication with the blood outlet 26, and a pumping means 4 for the driving accumulator 3 so as to deliver blood in the accumulator 3 to a downstream destination. The blood accumulator 3 is adapted to store blood in an amount proportional to the volume of blood reserved in the tank 2 at least when the volume of blood reserved in the tank 2 is below a predetermined value. The pumping means 4 is intermittently operated to drive the accumulator 3 so as to intermittently deliver blood therefrom. The pumping means 4 is controlled by a fluid feeder 5 for delivery.

As mentioned above, the blood accumulator 3 stores blood in an amount proportional to the volume of blood in the tank 2 when the volume of blood in the tank 2 is below the predetermined value and the pumping means 4 acts to intermittently deliver blood from the accumulator 3. As the residual blood volume in the tank 2 decreases, blood is accordingly delivered in a smaller amount. Even when the residual blood volume in the tank 2 is very small, delivery of a minor amount of blood is maintained. It is unnecessary to interrupt blood delivery when the residual blood volume in the tank 2 decreases, thereby avoiding blood stagnation in an extracorporeal blood circulation circuit.

The blood reservoir 10 includes the blood tank 2 and a blood delivery instrument 6 which includes the blood accumulator 3 and the pumping means 4.

Figure 2:
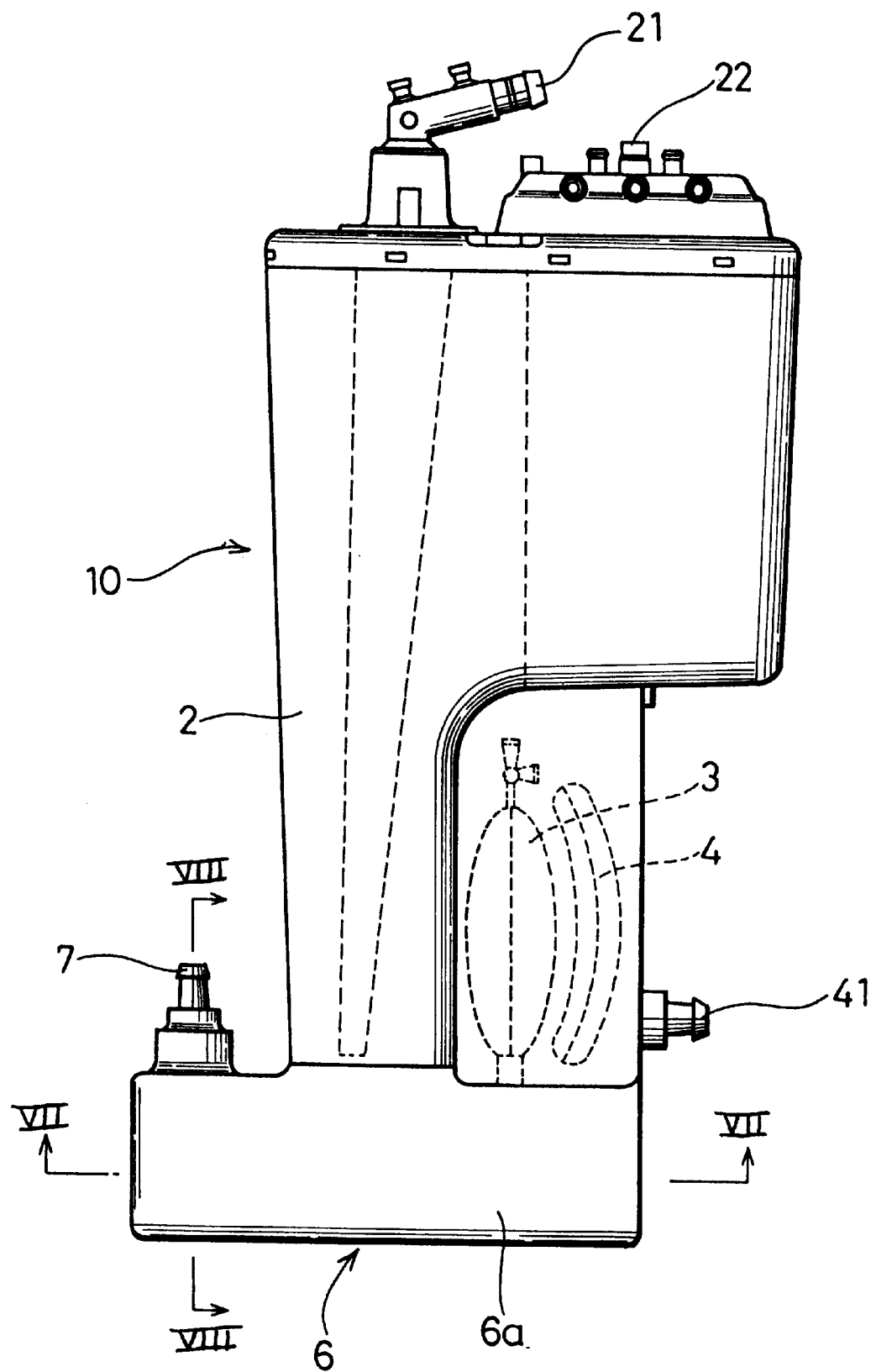
FIG. 2 is a front elevation of the blood reservoir according to the invention.
Figure 4:
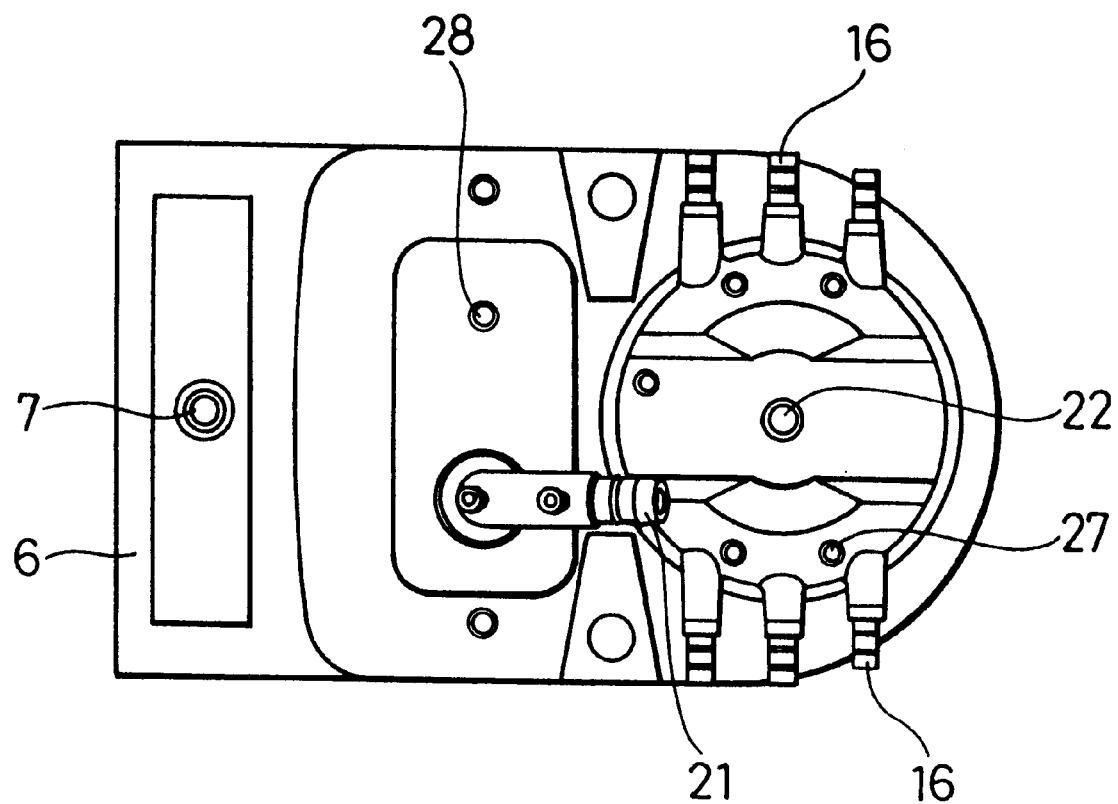
FIG. 4 is a top view of the reservoir of FIG. 2.
Figure 6:
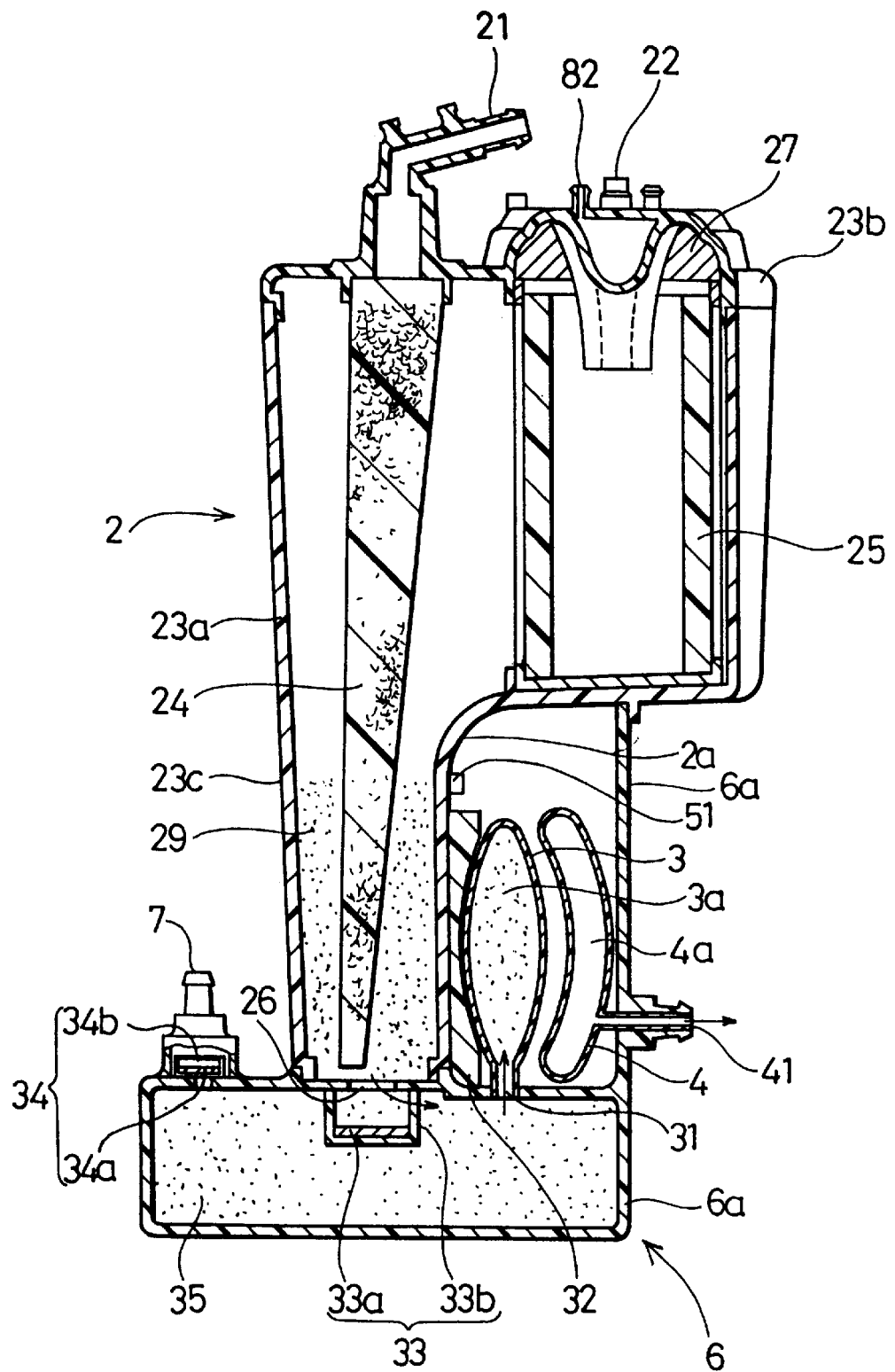
FIG. 6 is a cross-sectional view taken along lines VI—VI in FIG. 5.

As shown in FIG. 6, the blood tank 2 includes a tank housing consisting of a main body 23a and a cover 23b both made of rigid resin. The cover 23b is fitted on the top end of the housing main body 23a so as to cover the upper opening of main body 23a as shown in FIGS. 2 and 6. The cover 23b has blood flow inlets 21 and 22 and air vents 27 and 28 as shown in FIG. 4. The blood flow inlet 22 is connected to a cardiotomy line for feeding blood from the operation area. The blood flow inlet 21 is connected to a drainage line for feeding blood from a drainage cannula inserted into the heart ascending/descending veins of the patient. Received in the housing main body 23a are a cardiotomy blood filter 25 four filtering the blood incoming from inlet 22 and a venous blood filter 24 for filtering the blood incoming from the inlet 21.

The housing main body 23a has a downward projection 23c. The blood outlet 26 is formed in the bottom of the projection 23c.

The housing may be formed of any desired resin, for example, polyearbonate, acrylic resin, polyethylene terephthalate, polyethylene, polypropylene, polystyrene, polyvinyl chloride, acryl-styrene copolymers, and acryl-butadiene-styrene copolymers. Polycarbonatc, acryl resin, polystyrene, and polyvinyl chloride are especially preferred.

Figure 3:
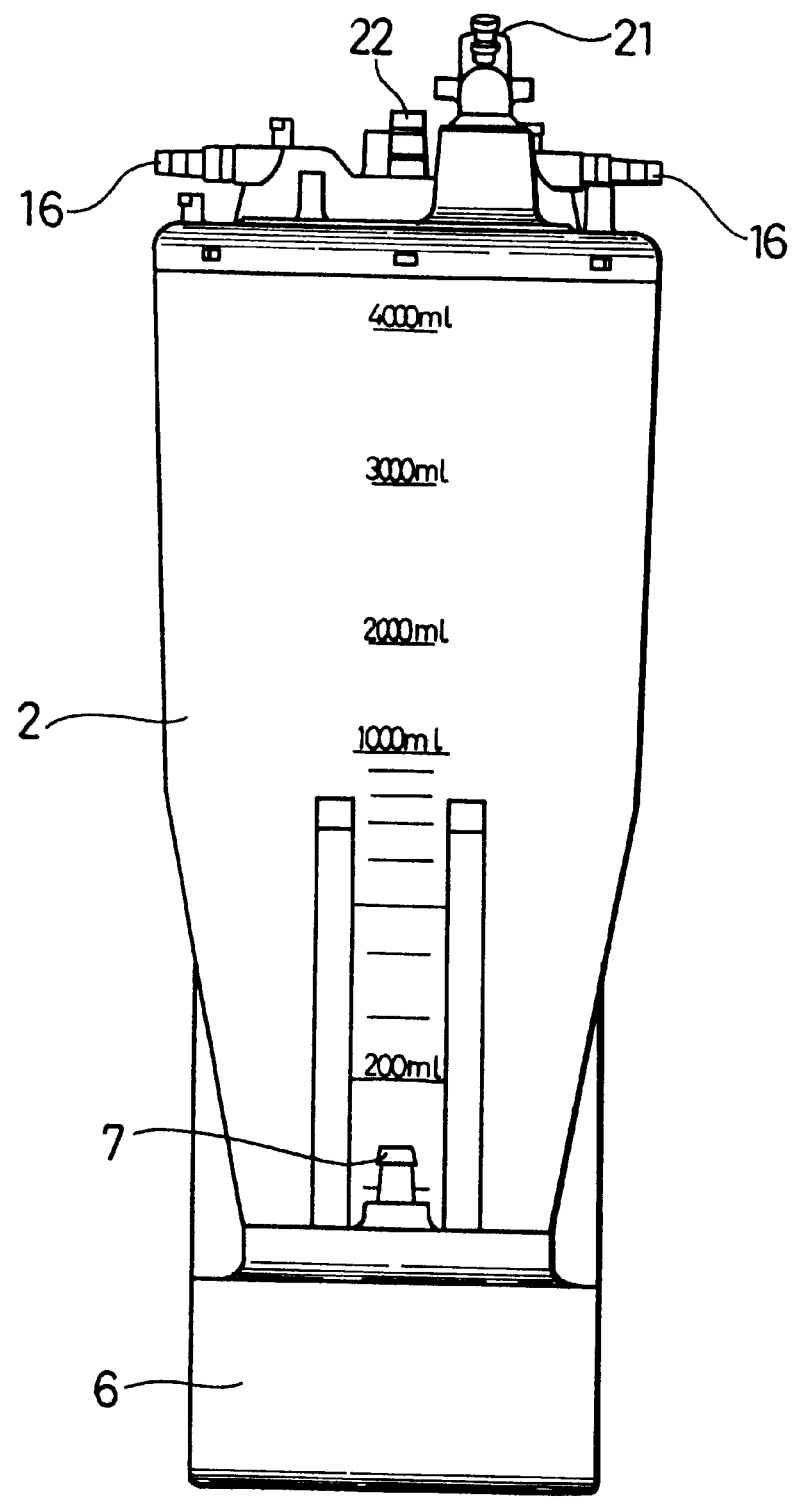
FIG. 3 is a left side view of the reservoir of FIG. 2.

Defined within the blood tank housing is a blood reserve portion 29 for temporarily reserving blood as shown in FIG. 6. The blood reserve portion 29 may have any desired volume although it generally has a volume of about 3,000 to 5,000 ml for adults and about 1,000 to 2,500 ml for children. The housing is preferably substantially transparent or semi-transparent, so that the volume or state of blood reserved may be readily ascertained. The downward projection 23c has a reduced horizontal cross-section so that when the volume of blood reserved lowers, the volume of blood reserved or a change thereof can be correctly and readily read. As shown in FIG. 3, the projection 23c is convergent downward, that is, has a cross-sectional area decreasing toward the bottom. Scale marks are printed on the outside wall of the projection 23c. The blood tank 2 may also be a flexible tank formed of flexible resin. In this case, the blood tank is of the closed type.

Attached at the bottom of the blood tank 2 is the blood delivery instrument 6 which includes a housing 6a joined to the tank housing 23a. The blood delivery instrument 6 fuirther includes the blood accumulator 3 and the blood delivery pumping means 4 received between the instrument housing 6a and the tank housing 23a. Disposed between the blood tank housing 23a and the blood accumulator 3 is a backing 32 for retaing the accumulator 3. The backing 32 has a side configured in conformity with one side shape of the accumulator 3 when the accumulator 3 is full of the maximum amount of blood.

A blood channel section 35 is defined by the blood delivery instrument 6 on its lower side and provides fluid communication between the interior 29 of the blood tank 2 and the blood accumulator 3. Disposed in proximity to the blood flow outlet 26 of the blood tank 2 is a first check valve 33 which permits blood passage from the blood tank 2 to the blood channel section 35 (and hence, the blood accumulator 3), but restricts or prohibits the blood passage in the opposite direction. This first check valve 33 flnctions as a flowpath control member for shutting off communication between the blood tank 2 and the accumulator 3 during operation of the pumping means 4 as will be described later. The blood delivery instrument 6 is provided with a blood exit port 7 in communication with the blood channel section 35. Disposed in proximity to the blood exit port 7 is a second check valve 34 which permits blood passage to a side downstream of the blood channel section 35 (and hence, downstream of the blood accumulator 3), but restricts or prohibits blood passage in the opposite direction. This second check valve 34 functions as a flowpath control member for shutting off blood flow from the downstream side into the accumulator side (and hence, blood channel side) when the pumping means 4 is inoperative as will be described later.

Each check valve 33, 34 has a disc-shaped movable valve body 33a, 34a and a cage 33b, 33b adapted to receive the valve body therein and formed with an opening for blood passage. The movable valve body 33a, 34a preferably has a specific gravity substantially equal to or slightly lighter than the specific gravity of blood so that the valve body may be fully responsive. For example, the valve body is made of expanded polyethylene and has a thickness of about 1 to 10 mm, especially 3 to 8 mm.

In another embodiment, the check valve takes the form of a movable valve body a part of which is fixedly secured to the housing. Preferably the movable valve body is slightly lighter than the specific gravity of blood and a hardness of about 3 to 7 on Shore A scale. For example, the valve body is made of styrene elastomer oil gel or silicone gel and has a thickness of about 1 to 5 mm.

The blood accumulator 3 is in fluid communication with the blood channel section 35 via a blood passage port 31 which is located below or at the lower end of the accumulator 3 and formed at a position of the same height as the lower end of the blood reserve portion 29 (the outlet 26) of the blood tank 2 in a vertical direction. The blood tank 2 has the blood reserve portion 29 and the outlet 26 located at a lower end portion thereof. The accumulator 3 is located upwards than the outlet 26. The blood accumulator 3 extends substantially vertically upward and substantially parallel to the projection 23c of the blood tank 2 in this embodiment.

The accumulator 3 is formed as a bag or bladder of flexible resin. Under the condition that blood accumulator 3 is set so as to extend upward and parallel to the projection 23c of the blood tank 2, if the surface of blood in the tank 2 is below the uppermost end of the interior of the accumulator 3, an amount of blood proportional to the blood surface in the tank 2 flows into the accumulator 3. Inversely, now that the maximum containment amount of the blood accumulator 3 remains unchanged, if the surface of blood in the tank 2 is above the uppermost end of the interior of the accumulator 3, this maximum containment amount of blood flows into the accumulator 3.

Differently stated, the blood accumulator 3 is a pressure sensitive container since a pressure proportional to the volume of blood reserved in the tank 2 is applied thereto. When the volume of blood in the tank 2 is above a predetermined value (or the surface of blood in the tank 2 is above the uppermost end of the interior of the accumulator 3 in the illustrated embodiment), the maximum containment amount of the accumulator 3 becomes preferential to the pressure exerted by the volume of blood in the tank 2 so that the accumulator 3 contains the maximum containment amount of blood. If the volume of blood in the tank 2 is below the predetermined value (or the surface of blood in the tank 2 is below the uppermost end of the interior of the accumulator 3 in the illustrated embodiment), the accumulator 3 exerts a pressure sensitive function to contain blood in an amount proportional to the volume of blood in the tank 2 (or the height of the blood surface in the tank 2). Thus, the accumulator 3 has the function of automatically storing blood in an amount proportional to the volume of blood in the tank 2 when the volume of blood in the tank 2 is below the predetermined value.

It is preferred that the blood accumulator 3 does not suck in blood by itself, in another parlance, does not have a self-shape-recovery ability. If the accumulator 3 is formed to a shape defining a certain internal cavity, the accumulator 3 will restore the original shape when blood stored therein is displaced by pumping member 4 and the compression load by the pumping member 4 is released. The restoring force creates a suction force to provide suction of blood from the tank side. Then the accumulator has a minimum blood containment amount below which the accumulator cannot exert the pressure sensitive function mentioned above. The minimum blood containment amount associated with the self recovery force should preferably be zero although its presence is acceptable if it is negligibly small. The preferred form of the blood accumulator is a flexible bag prepared by placing a pair of sheets in close plane contact with a tube to form the blood passage port 31 interposed at the lower end, and heat sealing the sheets along the periphery to define a sealed interior except for the tube. This bag has an internal volume of substantially zero as formed. Differently stated, it is preferred that when a load is applied to the blood accumulator so as to establish a state that the internal volume is substantially zero and then released, the blood accumulator maintains the substantially zero volume state. The maximum blood containment amount (simply maximum amount or maximum displacement) of blood accumulator 3 is preferably about 20 to 500 ml, more preferably about 50 to 300 ml, further preferably about 80 to 300 ml although the exact amount varies with the maximum volume of blood reserved in the blood tank combined therewith. It is preferred that the maximum blood containment amount of the accumulator 3 is greater than the volume of the channel section 35. Consequently, when blood is displaced from the accumulator 3, the entire volume of blood contained in the channel section 35 is displaced so that the stagnation of blood in the channel section 35 may be minimized.

The blood accumulator 3 in the illustrated embodiment is entirely formed of a flexible material and thus entirely deformable so that the accumulator 3 may be compressed and deformed when the blood delivery pumping means 4 is inflated. However, the blood accumulator is not limited to the entirely flexible one. It is acceptable that a portion of blood accumulator 3, for example, a portion of the blood accumulator 3 which comes in contact with the pumping means 4 is a deformable portion formed of a flexible material.

Blood contained in the accumulator 3 is displaced by the blood delivery pumping means 4 into the channel section 35 and then discharged to an outside destination through the exit port 7. When the volume of blood reserved in the tank 2 is smaller than the predetermined value, blood is delivered in an amount proportional to the residual volume of blood in the tank 2. As the residual volume of blood in the tank 2 becomes smaller, the amount of blood delivered is automatically reduced to a level approximate to zero, but not reduced to zero. That is, the blood reservoir 10 of the invention always maintains blood delivery though in a very small amount. Thus the interruption of blood delivery never occurs, preventing blood stagnation on a side of the extracorporeal blood circulation circuit downstream of the blood reservoir 10.

Since the blood accumulator 3 is a flexible bag, it provides a very low resistance to blood inflow and sensitivity to pressure variations so that blood may be contained in an amount fully proportional to the residual volume of blood in the tank 2. Moreover, the accumulator 3 is designed such that it contains the predetermined amount of blood in the duration when the volume of blood in the tank 2 is above the predetermined level, while the amount of blood contained in accumulator 3 varies in proportion of the residual volume of blood in the tank 2 in the duration when the volume of blood in the tank 2 is below the predetermined level. The maximum containment amount is fixed and this maximum containment amount of blood is contained when the volume of blood in the tank 2 is above the predetermined level. Then the amount of blood delivered by pumping means 4 in the normal state can be readily controlled in terms of the number of compressions or pulsations per unit time of accumulator 3 by pumping means 4. A substantially constant amount of blood is delivered per pulsation. Satisfactory pulsative blood flow can be easily established.

The blood accumulator is desired to be fully flexible. One index of flexibility is compliance. The blood accumulator preferably has a compliance of above 2 ml/sec·mHg, preferably 5 to 30 ml/sec·mHg when the surface of blood in the reserve portion of the tank 2 is lower than the uppermost end of the interior of the accumulator, differently stated, when the accumulator exerts a pressure (or blood level) sensitive function. Further preferably the blood accumulator reduces its compliance to a lower value when the surface of blood in the reserve section of the tank 2 is above than the uppermost end of the interior of the accumulator. The resistance of the accumulator to blood inflow can be expressed by an inflow rate of blood into the accumulator and the accumulator preferably has a blood inflow rate of 20 to 600 ml/sec.

Examples of the flexible resin include polyvinyl chloride, vinyl chloride-vinyl acetate copolymers, vinyl chloride-ethylene copolymers, vinyl chloride-vinylidene chloride copolymers, vinyl chloride-urethane copolymers, vinyl chloride-acrylonitrile copolymers, vinyl chloride-methyl methacrylate copolymers, and flexible polyvinyl chloride modified products comprising the foregoing polymers and plasticizers, and polyurethane.

Thermoplastic polyurethanes are especially preferred. The thermoplastic polyurethanes may be either thermoplastic polyether polyurethanes or thermoplastic polyester polyurethanes, with the thermoplastic polyether polyurethanes being preferred. Especially preferred are thermoplastic polyether polyurethanes comprising soft and hard segments. The soft segment is preferably formed from polytetra-methylenle ether glycol polyethylene glycol and poly-propylene glycol as a main component. The hard segment is preferably formed from 1,4-butane diol as a main component. The disocyanate includes 4,4-diphenylmethane diisocyanate, tolylene diisocyanate, and 1,6-hexamethylene diisocyanate. Most preferred polyurethane material is a thermoplastic segmented polyurethane which is formed using polytetra-methylene ether glycol as a main component of the soft segment, 1,4-butane diol as a main component of the hard segment, and 4,4-diphenylmethane diisocyanate as the diisocyanate. This polyurethane is commercially available under the trade name of Pelecene 2363 from Dow Chemical Co.

The surface of the accumulator which will be wetted with blood is preferably antithrombic. The antithrombic surface may be formed by applying and fixing an antithrombin to the surface. Exemplary antithrombins are heparin, urokinase, HEMA-St-HEMA copolymers, and poly-HEMA.

Preferably, the antithrombic surface is formed by treating a substrate with ozone to form functional group-bearing oxides on the substrate surface and applying heparin to the surface so that an amino group of heparin forms a covalent bond with the functional group directly or through a coupling agent. This method permits heparin to be fixed on the blood wetting surface without the use of a solvent, minimizing a change of physical properties (e.g., flexibility, elasticity and strength) of the substrate presenting the blood wetting surface.

Through ozone treatment, oxides are formed on the substrate surface and high reactive functional groups such as aldehyde, ketone, and epoxy groups are generated in the oxides. Amino groups of heparin can directly bond with these functional groups. For the reason of steric hindrance or other, introducing a spacer or coupling agent into these functional groups prior to fixation of heparin is easy and useful from the standpoint that the suffice allows heparin to develop its activity. The coupling agents may be used alone or in admixture of two or more. Compounds having at least two aldehyde or epoxy groups are preferred.

Where two or more coupling agents are used, the preferred sequence is by first bonding a coupling agent (spacer coupling agent) in the form of a compound having at least two amino groups with the functional groups previously introduced in the substrate, to thereby introduce amino acid into the substrate, and thereafter bonding heparin to the substrate with the aid of a coupling agent (heparin-fixing coupling agent) in the form of a compound having at least two aldehyde or epoxy groups. In bonding heparin, the coupling agent is preferably admitted into the reaction system at the same time as or subsequent to heparin admission.

Especially when an amino group is introduced using a spacer coupling agent, it displays substantially the same reactivity as the amino group of heparin in the reaction system so that subsequent fixation of heparin to the substrate by the heparin-fixing coupling agent may take place more effectively.

Where the functional group of a coupling agent to directly bond with heparin or the functional group introduced into the substrate is an aldehyde group, it is preferable to use heparin in which some N-suliate groups are desulfurized into primary amino groups.

The spacer coupling agent is one that forms a bond (covalent bond) with the functional group introduced on the substrate by ozone treatment and has at least two primary amino groups. Examples of the spacer coupling agent having at least two amino groups include polyethylene imine (PEI), polyethylene glycol diamine, ethylene diamine, and tetramethylene diamine Aldehyde and epoxy compounds are preferable as the coupling agent used for fixing heparin to the substrate. Exemplary of the aldehyde compound are glutaraldehyde, glyoxal, and succindialdehyde. Exemplary of the epoxy compound are polyethylene glycol diglycidyl ether, 1,4-butane diol diglycidyl ether, sorbitol diglycidyl ether, and glycerol diglycidyl ether. Illustrative examples are Denacol EX-421, 521, 611, 612, 614, and 614B where the epoxy compound is sorbitol diglycidyl ether; Denacol EX-313 where the diepoxy compound is glycerol diglycidyl ether; Denacol EX-810, 811, 851, 821, 830, 832, 841, and 861 where the diepoxy compound is polyethylene glycol diglycidyl ether, all commercially available from Nagase Chemicals K. K. Denacol EX-313, 421, 512, 521, 810, 811, 821, and 851 are preferred when the difference of epoxy reactivity is considered. In the above-mentioned heparin fixation, coupling-off of heparin is minimized since the bond between polyethylene imine fixed to the substrate and glutaraldehyde and the bond between glutaraldehyde and heparin are both covalent bonds.

Figure 9:
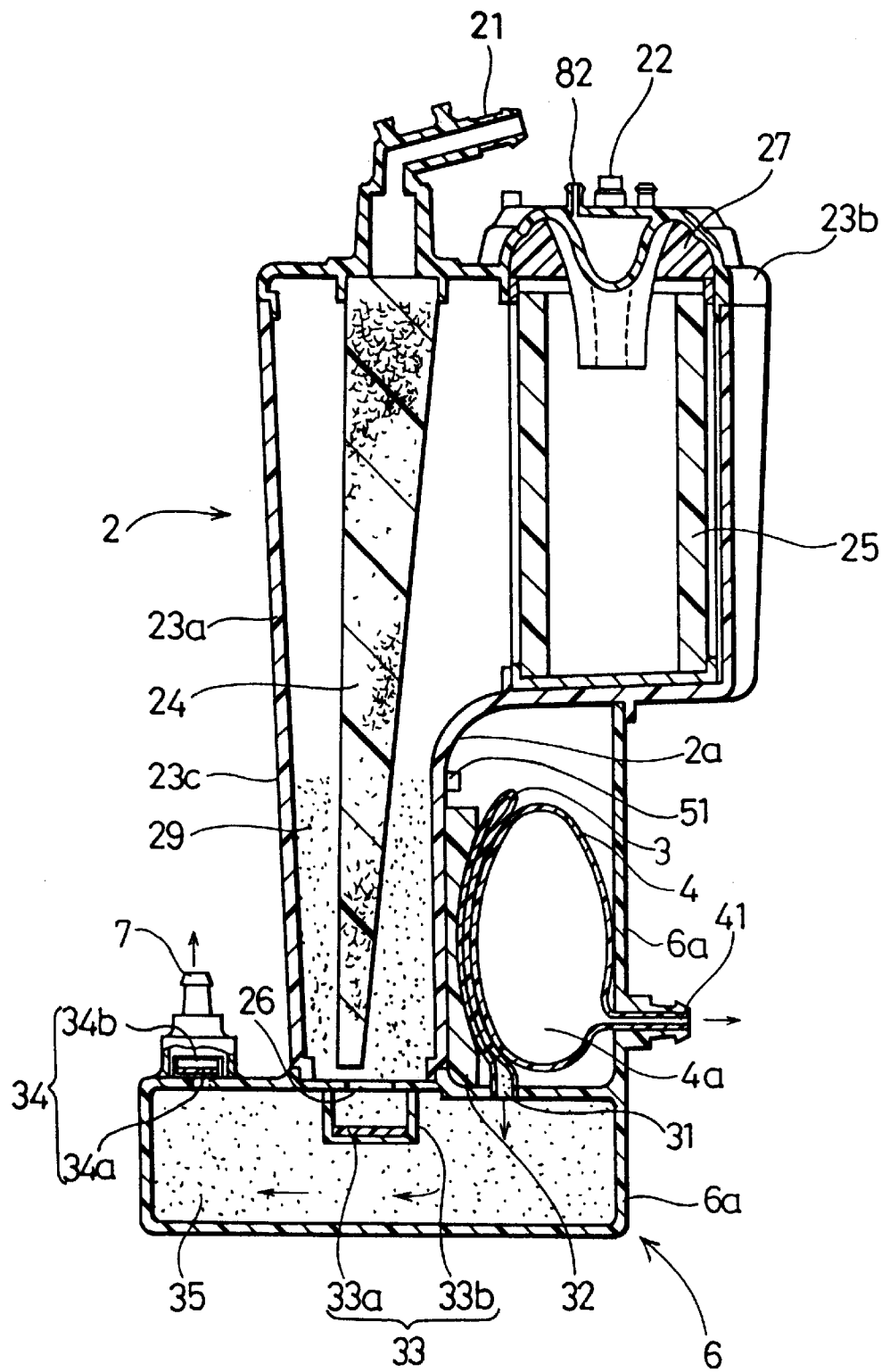
FIG. 9 is a schematic view for explaining the operation of the blood reservoir of the first embodiment.

Disposed between the accumulator 3 and a vertically extending side wall of the housing 6a of the blood delivery instrument 6 is the blood delivery pumping means 4. The pumping means 4 is preferably a flexible bag formed of a flexible resin as used in the accumulator and defining a fluid flow space 4a therein. The pumping means 4 is in fluid communication with a fluid flow port 41 in the housing side wall 6a of the blood delivery instrument 6. On use, the port 41 is connected to fluid feed unit 5 for feeding fluid for blood delivery as shown in FIG. 1. A compressor built in the fluid feeder unit 5 operates to feed or discharge an operative liquid or gas to or from the pumping bag 4 for expansion or contraction. Upon contraction, the pumping bag 4 does not contact the accumulator bag 3 as shown in FIG. 6. Upon expansion, the pumping bag 4 inflates as shown in FIG. 9 to compress the accumulator bag 3 against the backing 32 for displacing blood out of the accumulator bag 3. The containment for receiving the accumulator bag 3 (defined between the blood tank housing 23a and the blood delivery instrument housing 6a may be sealed substantially gas-tight. In this case, the containment is under positive pressure upon inflation of the pumping bag 4, but upon contraction of the pumping bag 4, the containment is kept under negative pressure which facilitates initial inlow of blood into the accumulator bag 3. Since the blood delivery pumping means 4 is in the form of a flexible bag which is inflated or contracted by feeding fluid into and out of the bag in the illustrated embodiment, it causes little damage to the accumulator 3 when compressing accumulator 3. Since the accumulator 3 has a deformable portion formed of flexible material and upon blood delivery, the pumping means 4 acts to deform that deformable portion to displace blood out of the accumulator 3, blood can be intermittently discharged from the accumulator 3 in an amount proportional to the volume of blood reserved in the blood tank 2.

The blood delivery pumping means 4 can regulate the amount of blood displaced out of the accumulator 3 by adjusting the amount or pressure of operative fluid introduced in the pumping means 4. The amount of blood to be displaced can be readily changed by setting a fixed number of driving actions of the pumping means 4 per unit time and adjusting the amount or pressure of operative fluid introduced in the pumping means 4. When the pumping means 4 is designed so as to displace blood out of the accumulator 3 while leaving some amount of blood therein, no excessive stresses are applied to the accumulator 3 and the sheets forning the accumulator 3 are not closely joined, preventing any obstruction against blood inflow into the accumulator 3 which would otherwise be caused by close junction.

Figure 10:
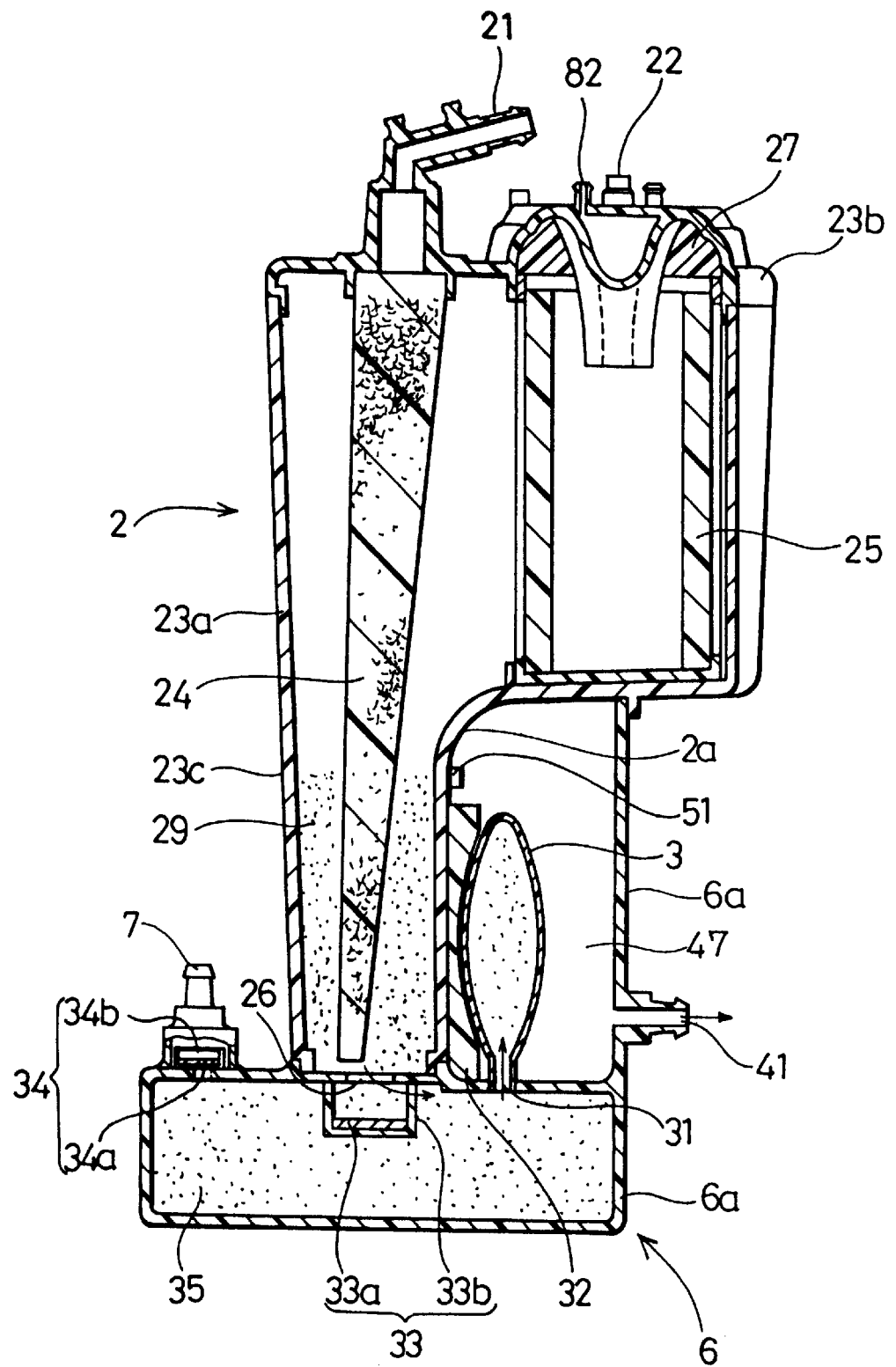
FIG. 10 is a cross-sectional view of a blood reservoir according to another embodiment of the invention.
Figure 11:
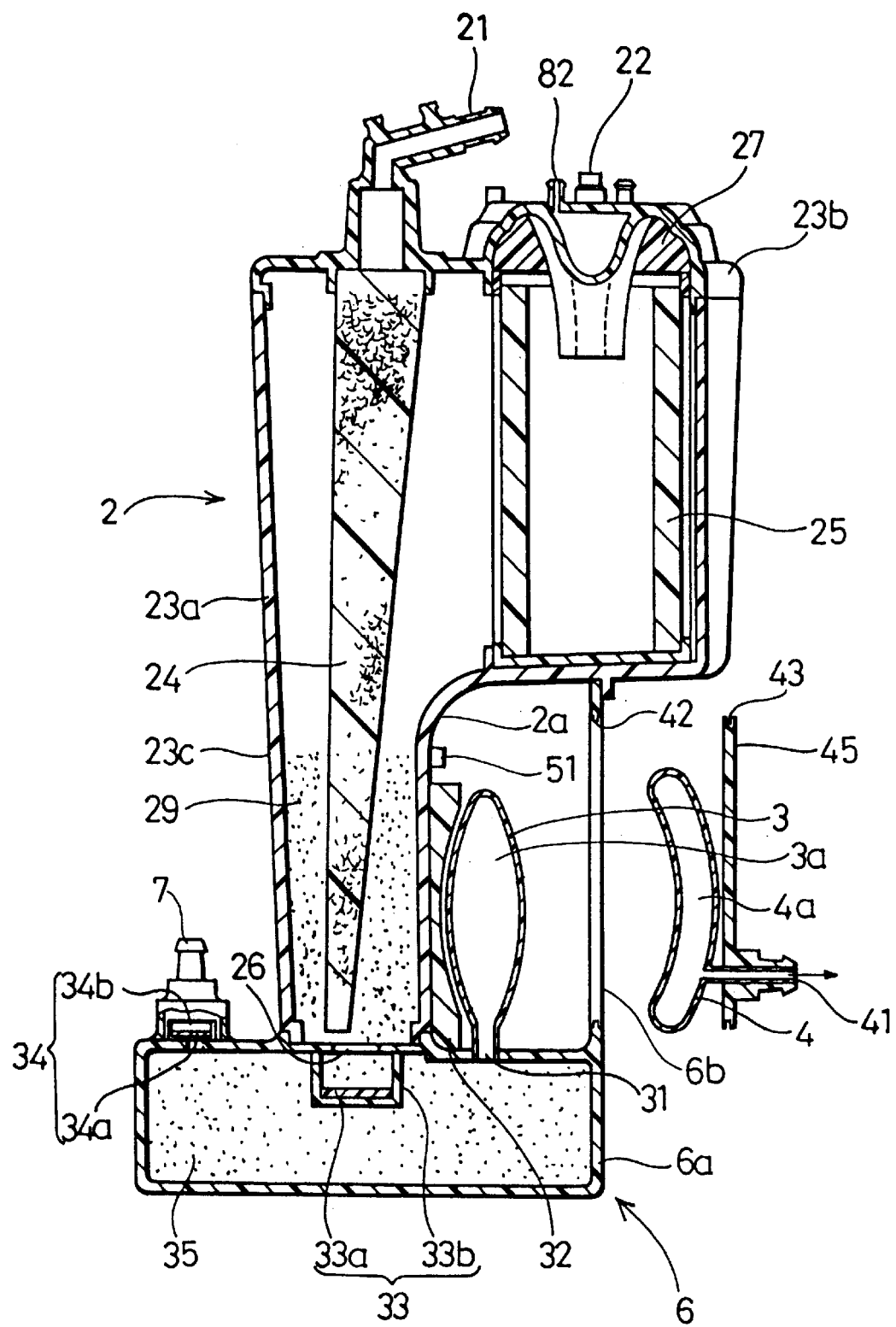
FIG. 11 is a cross-sectional view of a blood reservoir according to a further embodiment of the invention.

In another embodiment, a pumping bag or member can be omitted and pumping means of a different structure is constructed as shown in FIG. 10. In this embodiment, the containment 47 defined between the blood tank housing 23a and the blood delivery instrument housing 6a for receiving the accumulator 3 is sealed substantially gas-tight. The communication port 41 is connected to a pressurizing means in the form of a blood delivery fluid feed unit. A compressor built in the fluid feed unit 5 operates to feed or discharge an operative liquid or gas to or from the containment 47 so that the accumulator 3 itself repeats expansion or restoring contraction In the illustrated embodiments, the blood reservoir including the pumping means 4 is disposable as a whole. The invention is not limited to these embodiments. As shown in FIG. 11, the blood delivery pumping means 4 is removable from the blood reservoir since the pumping means 4 does not contact blood. The blood reservoir 10 of this embodiment does not have the pumping means 4 and the port 41 as integral components and instead, has an attachment therefor. More particularly, a blood delivery drive assembly including a plate member 45 provided with the port 41 and the pumping means 4 is separately furnished. The plate member 45 is attached to an opening 6b in the instrument housing 6a. The plate member 45 is provided with the engagements 43 and the instrument housing 6a is provided with the engagements 42. Through these engagements, the plate member 45 (or the blood delivery drive assembly) is tightly attached to the reservoir 10 so that the assembly may not be readily removed.

Figure 5:
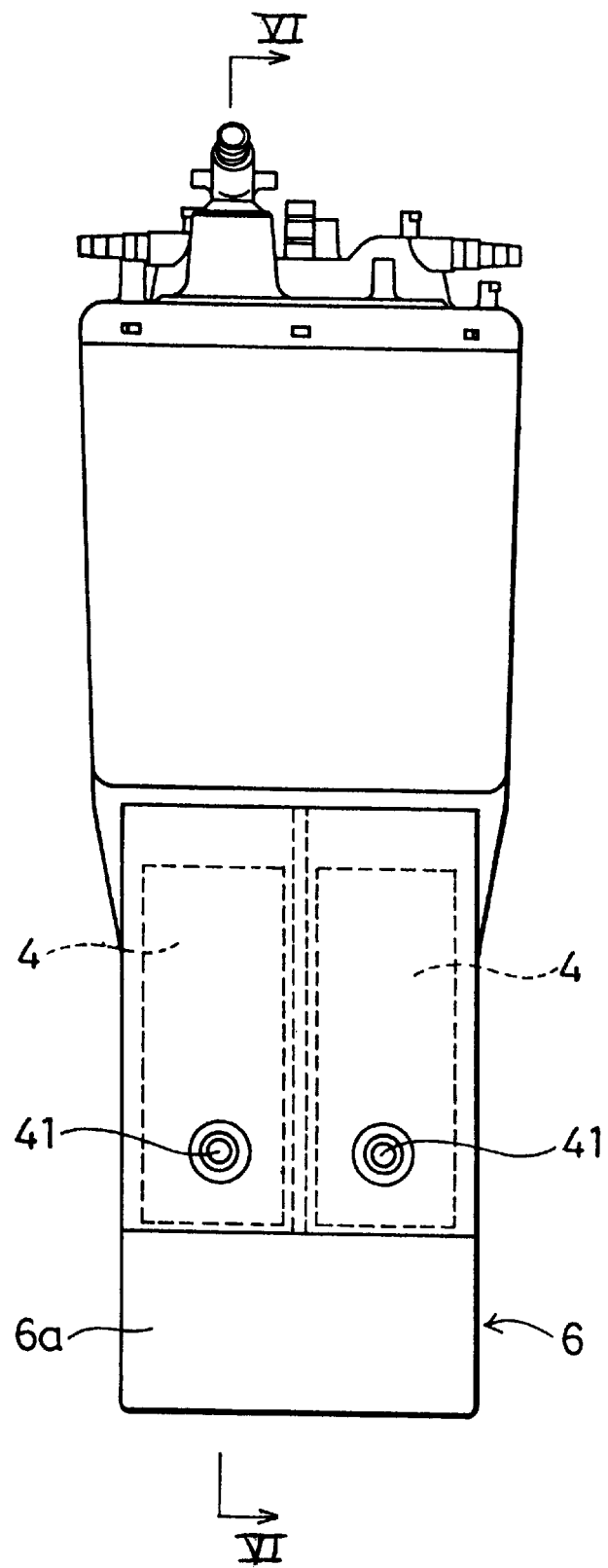
FIG. 5 is a right side view of the reservoir of FIG. 2.
Figure 7:
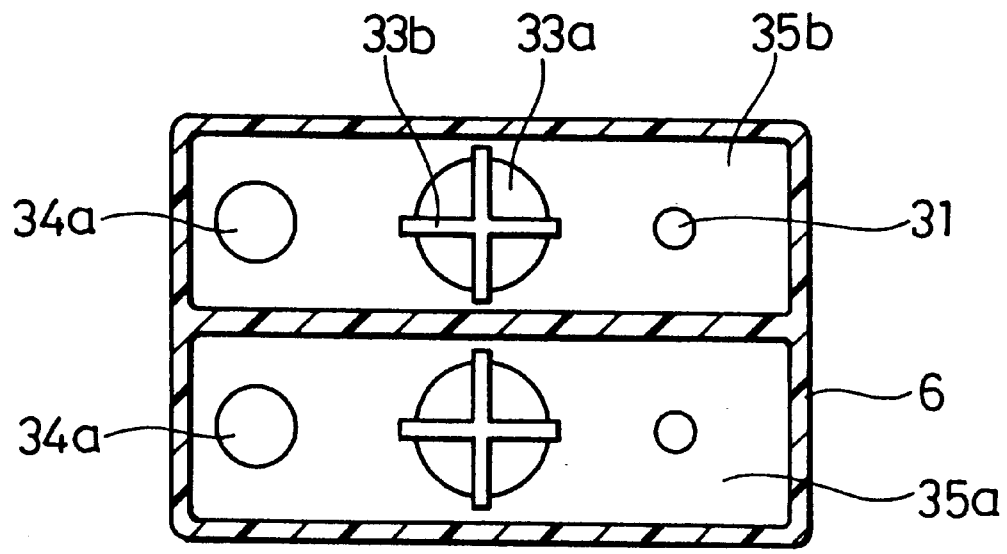
FIG. 7 is a cross-sectional view taken along lines VII—VII in FIG. 2.
Figure 8:
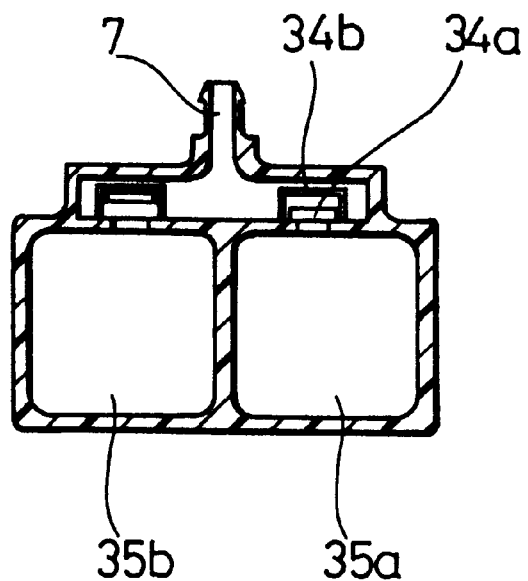
FIG. 8 is a cross-sectional view taken along lines VIII—VIII in FIG. 2.

As seen from FIG. 5, the blood reservoir 10 of the illustrated embodiment has two sets of the accumulators 3 and the pumping means 4. The blood channel 35 is also partitioned into two blood channels 35a and 35b which are not in fluid communication with each other as shown in FIGS. 7 and 8. When two or more sets of the accumulators 3 and the pumping means 4 are provided, the volume of each the accumulator 3 and the pumping means 4 is reduced so that the response of blood inflow and outflow is improved. If expansion timing is shifted between two pumping means 4, there can be formed a better blood flow. Despite shifted expansion timing between two pumping means 4, it never happens that blood flows from one accumulator to the other accumulator since two blood channels 35a and 35b are not in fluid communication with each other and each accumulator has an independent blood channel. The invention is not limited to the illustrated embodiment. The accumulator 3 and the pumping means 4 may be provided one set or three or more sets. Although the bag adapted to undergo repetitive inflation and contraction under the action of operative fluid is used as the pumping means 4 in the illustrated embodiment, the invention is not limited thereto. For example, a mechanism including a pressure plate 87 in contact with one side of a blood accumulator wherein the pressure plate is mechanically driven against the blood accumulator may be used as in the blood delivery apparatus shown in FIG. 13 to be described later.

In the illustrated embodiment of the blood reservoir 10 comprising two sets of accumulators 3 and pumping means 4 and a blood delivery fluid feed unit having a control ability to independently drive the pumping means 4, the form of blood flow to be delivered can be selected between a pulsative flow and a constant flow by taking into account the state of the patient and the artificial lung associated with the circulation line. Additionally the mode of blood flow to be delivered can be changed during operation. In the illustrated embodiment comprising two sets of accumulators 3 and pumping means 4, a substantially constant blood flow is obtained as a whole when the phases of blood flows delivered from the respective channels are shifted approximately 180 degrees, differently stated, when the phases of fluid flows discharged into or out of the pumping means 4 for blood delivery are shifted approximately 180 degrees Inversely, a pulsative blood flow is obtained when the phases of blood flows delivered from the respective channels are the same or ±30 degrees, differently stated, when the phases of fluid flows discharged into or out of the pumping means 4 for blood delivery are the same or ±30 degrees. Where three or more sets of accumulators 3 and pumping means 4 are provided, a substantially constant blood flow is obtained when the phases of blood flows delivered from the respective channels are shifted an angle of 360° divided by the number of sets.

Figure 12:
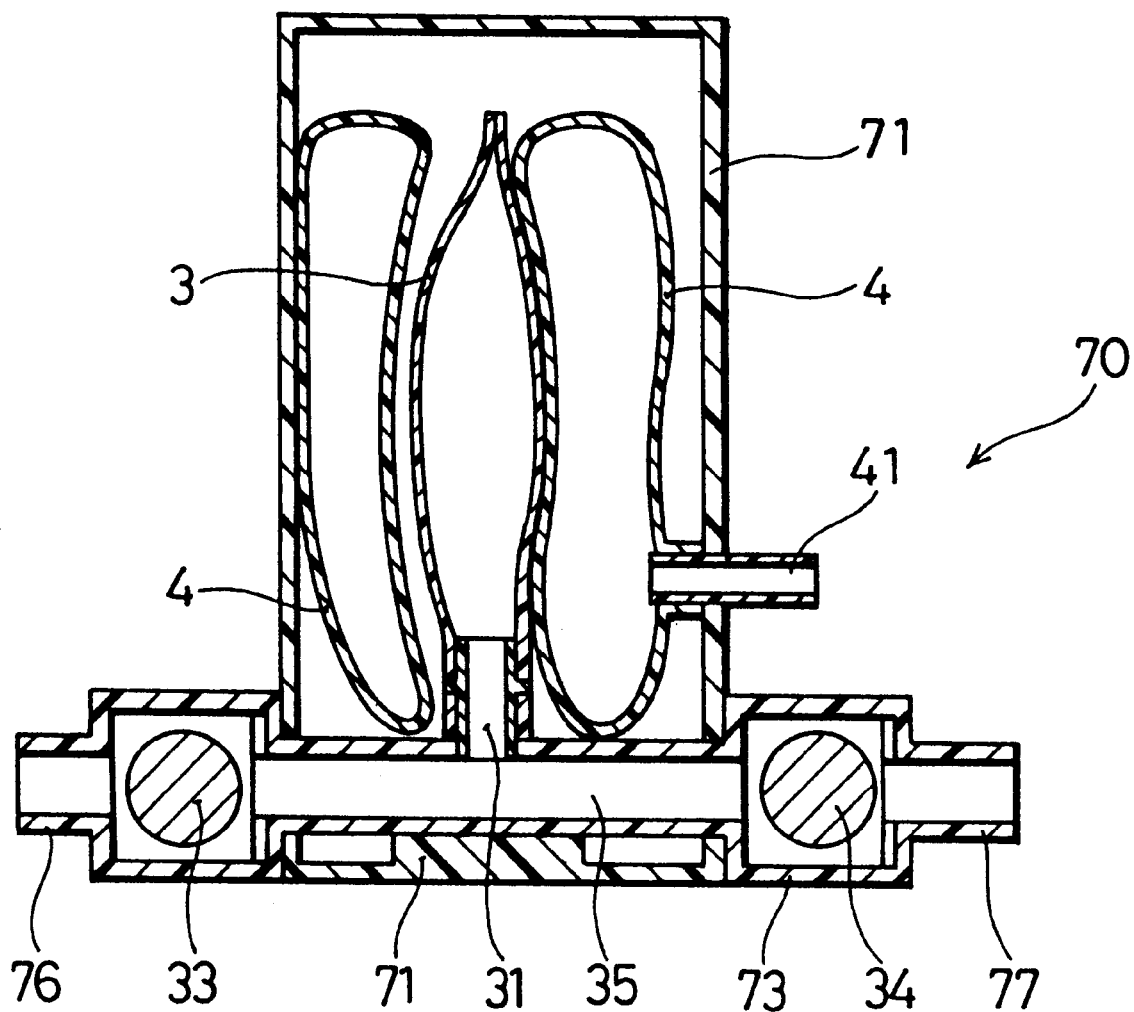
FIG. 12 is a cross-sectional view of a blood delivery instrument according to one embodiment of the invention.

FIG. 12 illustrates a blood delivery instrument 70 according to the invention.

This blood delivery instrument 70 is used in an extracorporeal blood circulation circuit having a blood tank. The blood delivery instrument 70 includes a blood accumulator 3 in communication with a blood outlet of the tank and a pumping means 4 for driving accumulator 3 to deliver blood from the accumulator 3 outward. As in the first-mentioned embodiment, the blood accumulator 3 serves to temporarily store blood in an amount proportional to the volume of blood reserved in the tank 2 when the volume of blood in the tank 2 is below a predetermined value. The pumping means 4 serves to intermittently drive the accumulator 3 so as to displace blood therefrom.

The blood delivery instrument 70 includes an accommodating housing 71 having the accumulator 3 and the pumping means 4 received therein and a channel housing 73 disposed below the housing 71 and defining a blood channel 35 therein. The channel housing 73 has at one end a blood inlet port 76 connected to the outlet of the blood tank and at another end a blood outlet port 77. The accommodating housing 71 has a bottom configured to attach the channel housing 73 thereto and defines an interior space where the accumulator 3 and the pumping means 4 are received. The accumulator 3 and pumping means 4 may be the same as in the first-mentioned embodiment.

The blood accumulator 3 is in fluid communication with the blood channel 35 defined in the housing 73 through a blood passage port 31. Disposed in proximity to the inlet port 76 of housing 73 is a first check valve 33 which permits blood flow from the blood tank side to the blood channel 35 side (and hence, to the accumulator 3), but restricts reverse blood flow. Disposed in proximity to the outlet port 77 of the housing 73 is a second check valve 34. The check valves illustrated in the figure are ball valves. The interior of the pumping means 4 is in fluid communication with a port 41 for passing a blood delivery operative fluid.

In this embodiment, pumping means 4 is configured to the contact accumulator 3 at opposite surfaces. More particularly, pumping bag 4 is folded and the accumulator bag 3 is interposed between the folded sections. Alternatively, the pumping bag 4 is formed in doughnut shape and the accumulator bag 3 is disposed at the center. The pumping bag 4 in contact with substantially the entire surface of the accumulator bag 3 ensures effective displacement of blood from the accumulator bag 3.

Next, the blood delivery fluid feed unit 5 shown in FIG. I is described.

The blood delivery fluid feed unit 5 is connected to the blood reservoir 10 through a tube 57 connected to the passage port 41 in communication with the pumping means 4. The fluid feed unit 5 has a fluid pump built therein for discharging a liquid (e.g., water and physiological saline) or gas (e.g., air) into and out of the pumping means 4 to intermittently repeat inflow and outflow of the fluid. The fluid feed unit 5 has a front panel including a switch section 52 having an input switch for setting a blood flow rate per unit time (e.g., a blood flow rate per minute) and/or an input switch for setting the number of pulsations per unit time (e.g., number of pulsations per minute). A display section 54 is to display the input blood flow rate and number of pulsations. The fluid feed unit 5 has built therein a computer which when a blood flow rate is input, computes the number of pulsations per unit time by considering the maximum capacity of the accumulator 3 (the amount of blood contained in the accumulator when the residual volume of blood in the blood tank is above a predetermined value) and delivers the computed result to the display section. Since the blood reservoir of the illustrated embodiment has two sets of accumulators and pumping means, the number of pulsations per unit time for each accumulator is one-half of the computed number of pulsations. Inversely, when a number of pulsations per unit time (e.g., a number of pulsations per minute) is input, a blood flow rate per unit time is computed by considering the maximum capacity of accumulator 3 and displayed at the display section.

The blood reservoir 10 has a level sensor 51 which is electrically connected to fluid feed unit 5, especially a lamp 56 through a control circuit. The level sensor 51 is attached to the blood tank 2 at a position corresponding to or slightly above the top end of the interior of the accumulator 3. When the level sensor 51 detects that the surface of blood is below the sensor 51, the lamp 56 flickers to indicate a blood delivery amount control mode. At the same time, any flow rate indication on the display section 55 disappears.

It is understood that blood delivery fluid feed unit 5 is applicable to all the illustrated embodiments.

The blood delivery fluid feed unit is not limited to the above-mentioned one. Another exemplar blood delivery fluid feed unit is shown in FIG. 32. This unit includes a display section 161 for displaying the flow rate detected by a flow rate sensor located downstream of the blood reservoir, a knob 162 for setting the pressure of blood delivery operative fluid, a display section 163 for displaying the pressure of blood delivery operative fluid, and a mode switch 164 for selecting a blood flow mode between a constant flow and a pulsative flow. While the number of pulsations of pumping blood delivery operative fluid per unit time is fixed, a knob is manually operated to adjust the pressure of blood delivery operative fluid for thereby adjusting the flow rate of blood. That is, this blood delivery fluid feed unit is to adjust the flow rate of blood by adjusting the force of the pumping means compressing the accumulator for thereby adjusting the amount of blood displaced from the accumulator (the amount of blood discharged from the blood contained in the accumulator).

Figure 13:
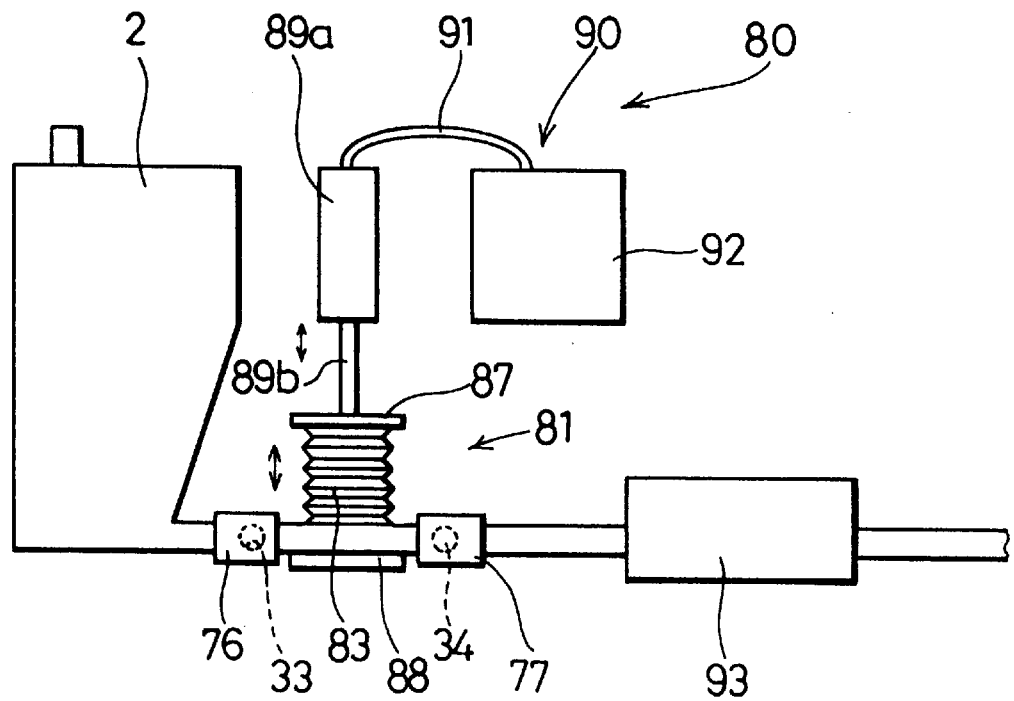
FIG. 13 is a schematic view of a blood delivery apparatus according to one embodiment of the invention.

FIG. 13 shows a blood delivery apparatus according to another embodiment of the invention.

This blood delivery apparatus 80 includes a blood delivery means 81 and a compression means 90. The blood delivery means 81 includes a blood channel having at one end a blood inlet port 76 connected to a blood outlet of a blood tank 2 and at another end a blood outlet port 77. The blood delivery means 81 further includes an accumulator 83 in fluid communication with the blood channel. The accumulator 83 is constructed as a vertically contractible bellows. The accumulator 83 in the form of a bellows is adapted to contain blood in an amount proportional to the volume of blood reserved in the blood tank when the volume of blood reserved in the blood tank is below the predetermined value. That is, when the volume of blood reserved in the blood tank is below the predetermined value, the top end of the accumulator bellows 83 lowers in accordance with the surface of blood in the blood tank.

The accumulator bellows 83 has a flat top end on which a pressure plate 87 is rested T he pressure plate 87 is fixedly secured to a piston rod 89b of a cylinder 89a to construct a blood delivery pumping means. The cylinder 89a is coupled to a hydraulic or pneumatic pressure generator 92 through a conduit 91 so that piston rod 89b is vertically moved by the operation of the generator 92. When the piston rod 89b is moved down, the pressure plate 87 urges the accumulator 83 downward. The accumulator bellows 83 is squeezed between the pressure plate 87 and a support plate 88 to reduce its interior volume to displace the blood therefrom to the channel and then to an artificial lung 93. Disposed in proximity to the inlet port 76 is a first check valve 33 which permits blood flow from the blood tank side to the blood channel side (and hence, to the accumulator 83), but restricts reverse blood flow. Disposed in proximity to the outlet port 77 is a second check valve 34. The check valves illustrated in the figure are ball valves.

Figure 14:
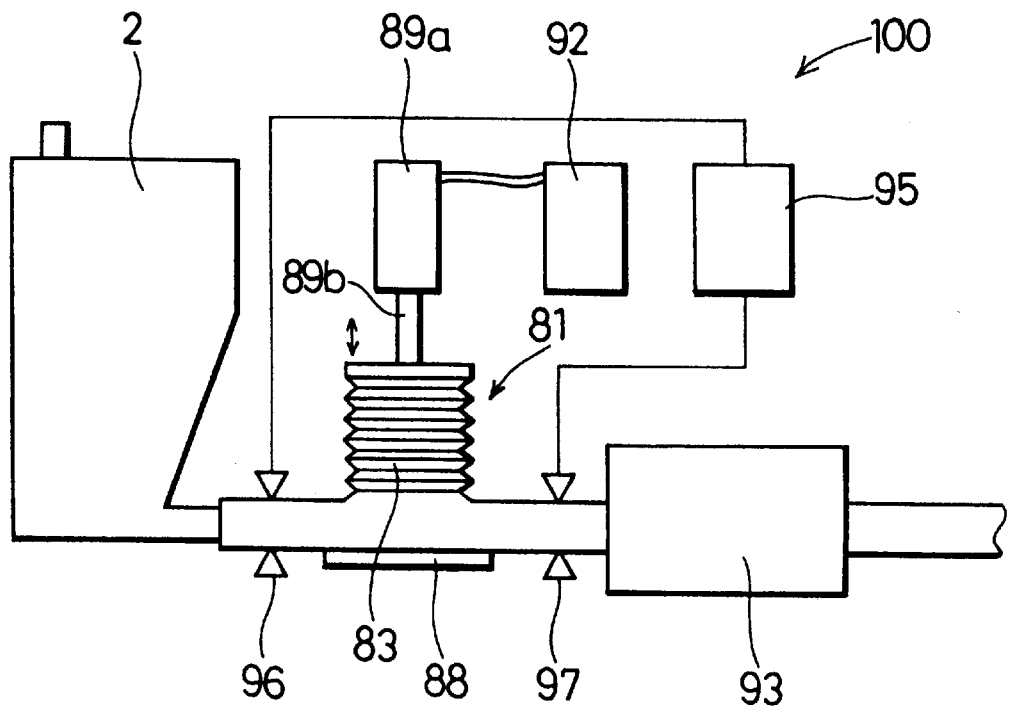
FIG. 14 is a schematic view of a blood delivery apparatus according to a further embodiment of the invention.

FIG. 14 shows a blood delivery apparatus according to a still further embodiment of the invention. The basic construction of this blood delivery apparatus 100 is the same as the foregoing apparatus 80. The difference resides in the use of flowpath control means instead of the check valves.

This blood delivery apparatus 100 includes a blood delivery means 81 and a compression means. The blood delivery means 81 includes a blood channel having at one end a blood inlet port connected to a blood outlet of a blood tank 2 and at another end a blood outlet port. The blood delivery means 81 further includes a accumulator 83 in fluid communication with the blood channel The accumulator 83 is constructed as a vertically contractible bellows. The accumulator 83 in the form of a bellows is adapted to contain blood in an amount proportional to the volume of blood reserved in the blood tank when the volume of blood reserved in the blood tank is below the predetermined value. The accumulator bellows 83 has a flat top end on which a pressure plate is rested. The pressure plate is fixedly secured to a piston rod 89b of a cylinder 89a to construct a blood delivery pumping means. The cylinder 89a is coupled to a hydraulic pressure generator 92 through a conduit so that the piston rod 89b is vertically moved by the operation of the generator 92. When the piston rod 89b is moved down, the pressure plate urges the accumulator bellows 83 downward. The accumulator bellows 83 is squeezed between the pressure plate and a support plate 88 to reduce its interior volume to displace the blood therefrom to the channel and then to an artificial lung 93.

Disposed in proximity to the inlet port is a first flowpath control means 96 in the form of a clamp with an electromagnetic valve, for example. Disposed in proximity to the outlet port is a second flowpath control means 97. These flowpath control means 96 and 97 and the hydraulic pressure generator 92 are connected to a controller 95. The controller 95 controls so as to render first flowpath control means 96 operative to shut off the flowpath to establish blockage between the accumulator 83 and the blood tank 2 when the piston rod is on a downward stroke (the pressure plate is moved down). When the piston rod is on an upward stroke (the pressure plate is moved up), the controller 95 controls the second flowpath control means 97 operative to shut off the flowpath to prevent blood entry into the accumulator 83 from a downstream side.

Figure 16:
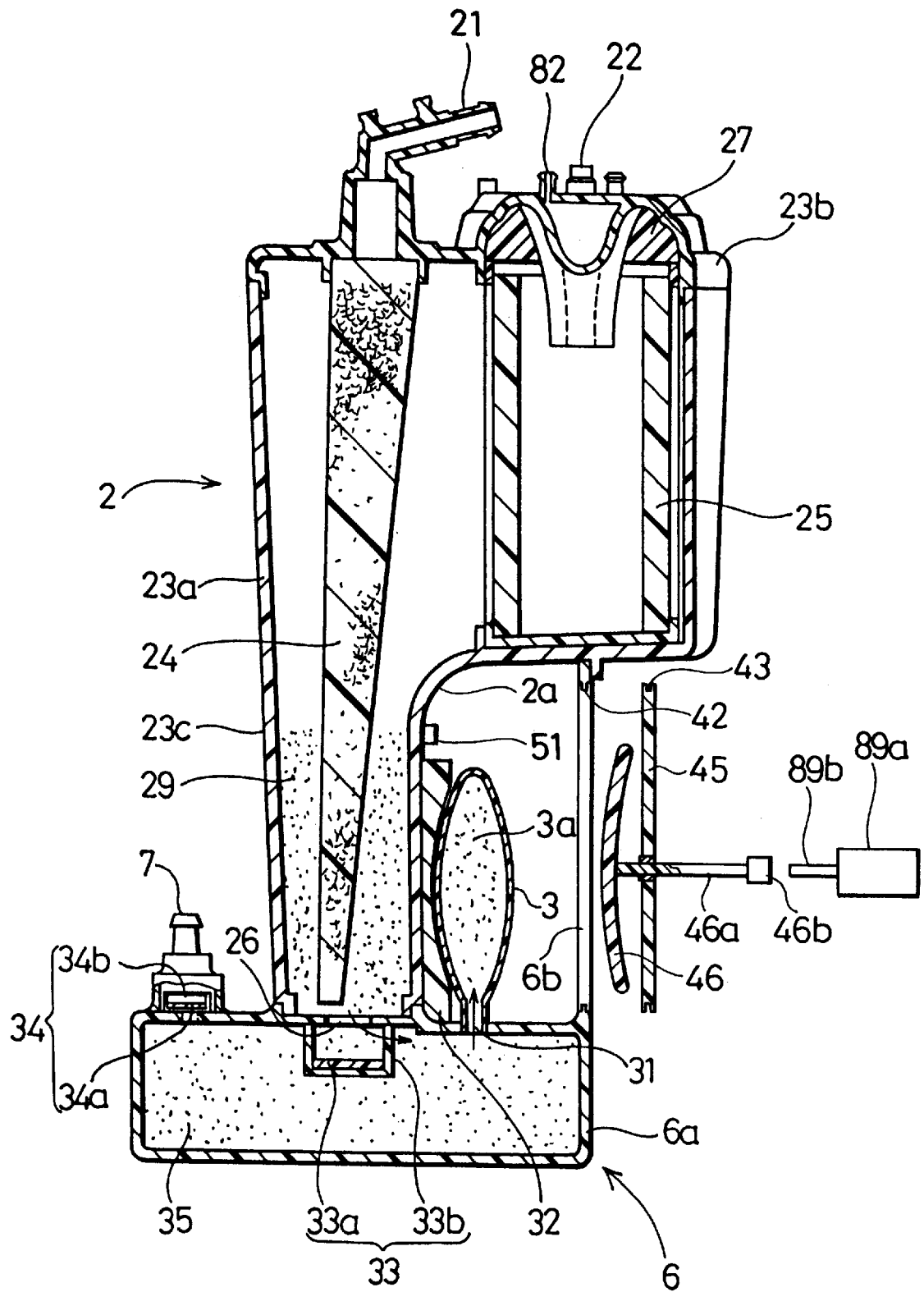
FIG. 16 is a cross-sectional view of a blood reservoir according to a still further embodiment of the invention.

FIG. 16 shows a blood delivery apparatus according to a still further embodiment of the invention.

The basic construction is the same as the apparatus shown in FIG. 11. The blood delivery pumping means is removably attached to the blood reservoir since the pumping means does not contact blood. The blood reservoir 10 of this embodiment does not have a pumping means as an integral component and instead, has an attachment therefor. More particularly, a blood delivery drive assembly including a plate member 45 and a pumping means is separately furnished The plate member 45 is attached to an opening 6b in the channel section housing 6a. The plate member 45 is provided with the engagements 43 and the channel section housing 6a is provided with the engagements 42. Through these engagements, the plate member 45 (or the blood delivery drive assembly) is tightly attached to the reservoir 10 so that the assembly may not be readily removed. The blood delivery drive assembly includes the pumping means in the form of a curved press plate 46 which is secured to one end of a drive shaft 46a extending through the plate member 45. The drive shaft 46a at another end is provided with a piston rod connector 46b through which the drive shaft 46a is removably connected to a piston rod 89b of a cylinder 89a. When the piston rod 89b is moved to the left in FIG. 16, the pressure plate urges and collapses the accumulator bag 3 to reduce its internal volume to displace blood therefrom. The thus displaced blood flows to an artificial lung side. The cylinder 89a is coupled to a hydraulic pressure generator (not shown) for driving the piston rod.

Figure 17:
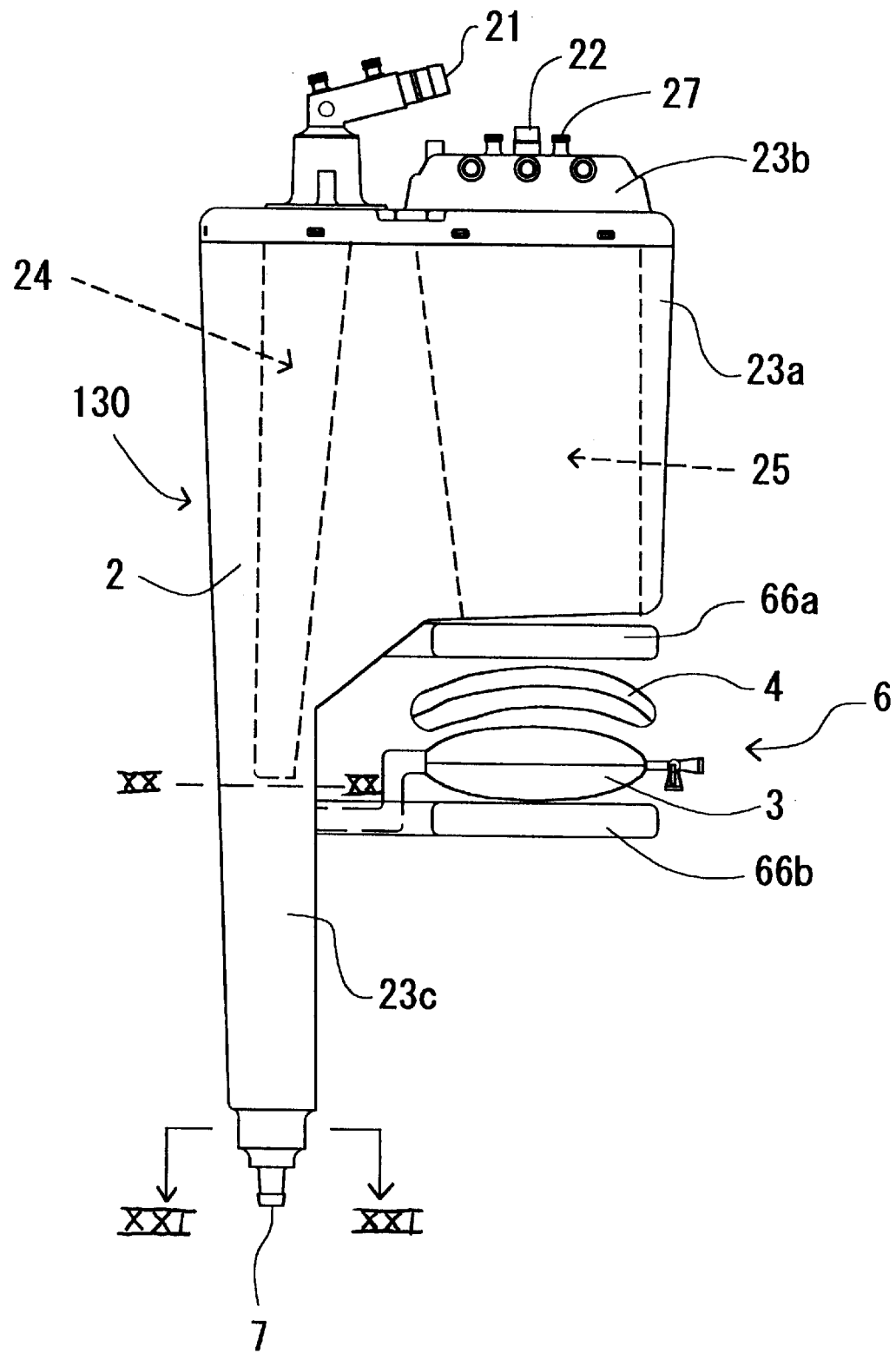
FIGS. 17 to 23 show a blood reservoir according to a further embodiment of the invention.
Figure 18:
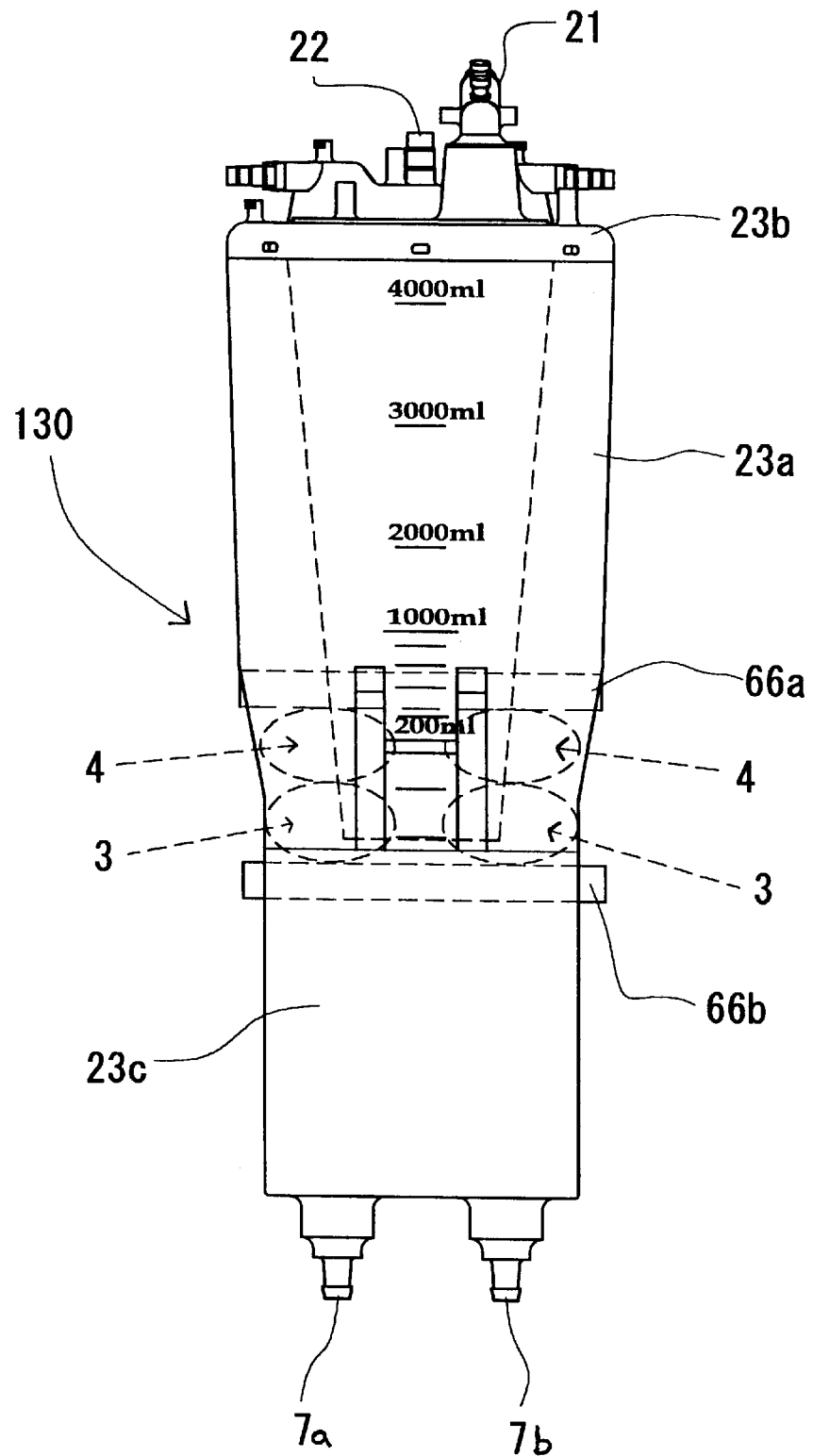
Figure 19:
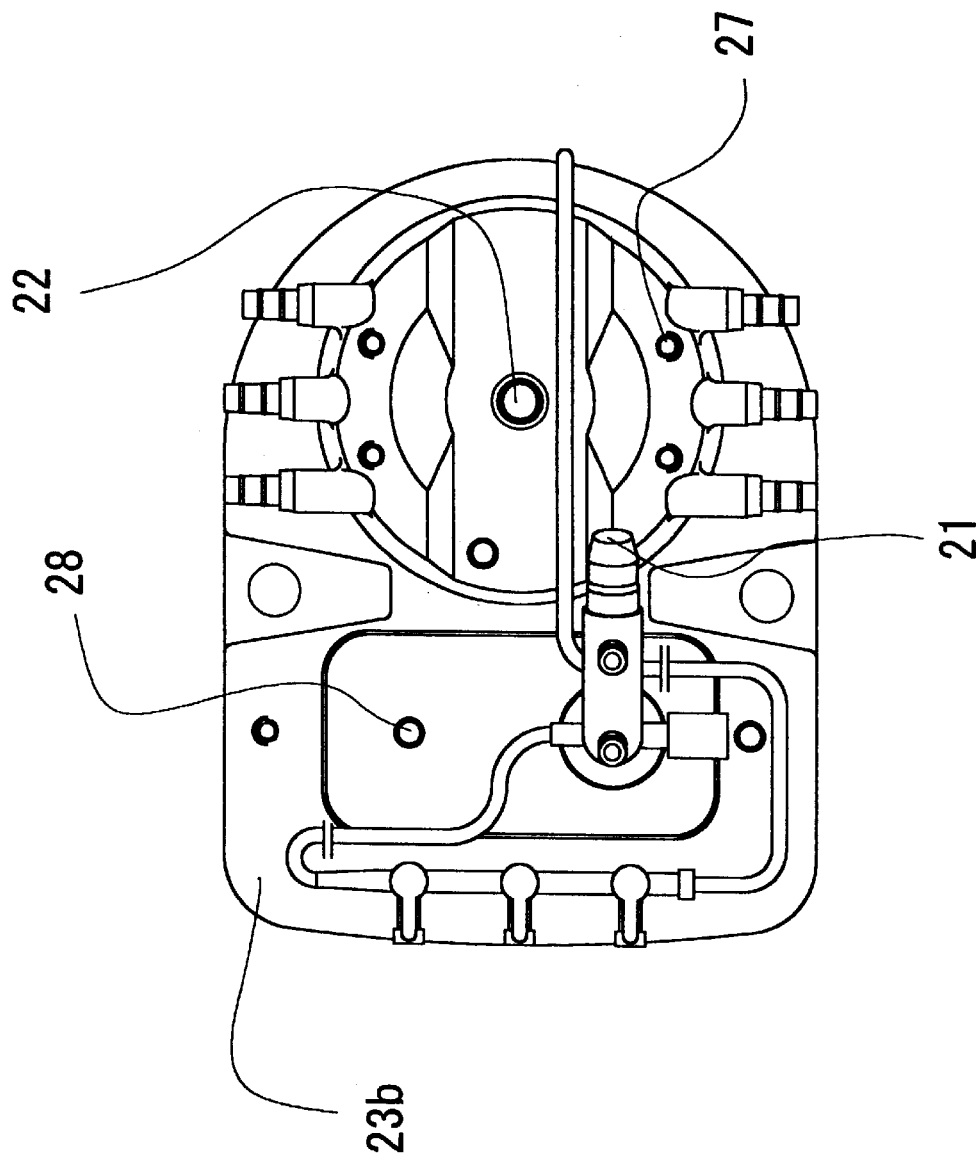
Figure 20:
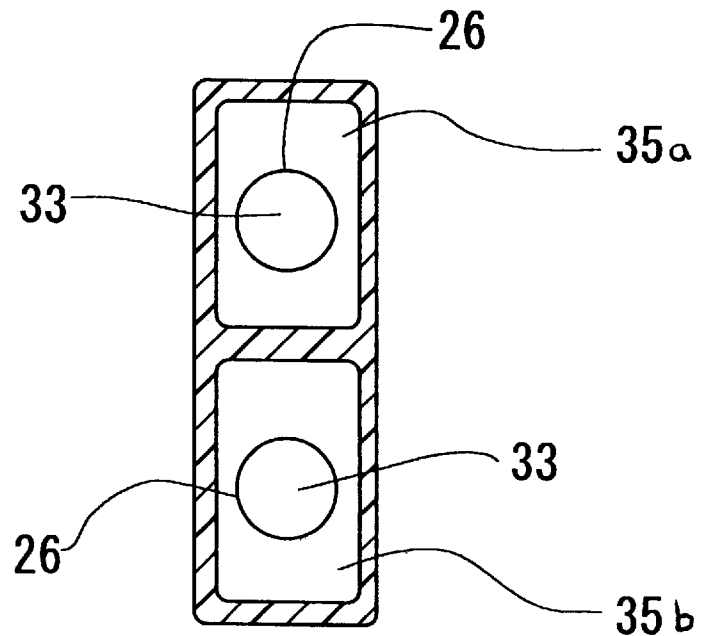
Figure 21:
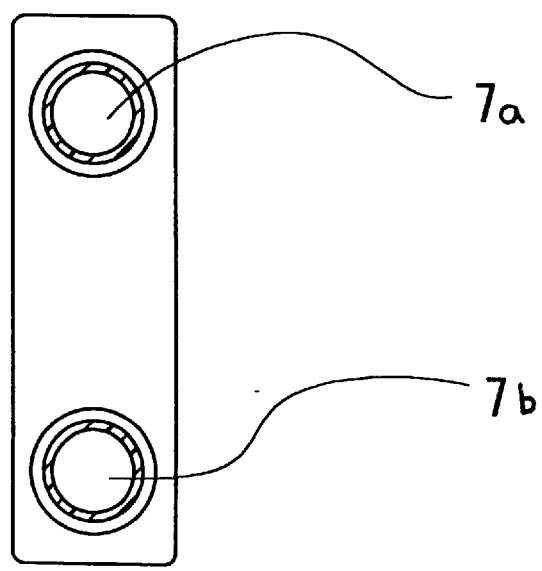
Figure 22:
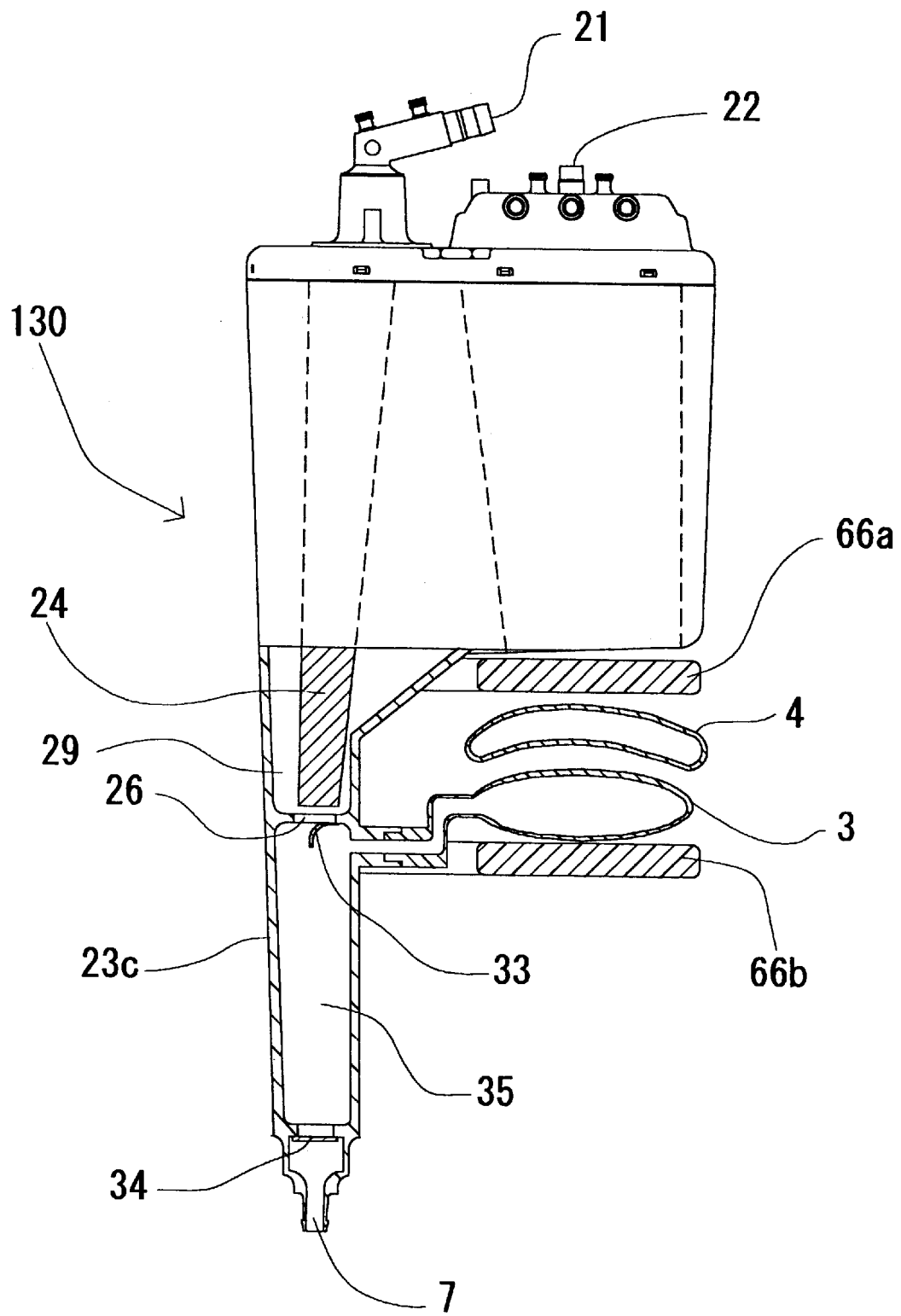
Figure 23:
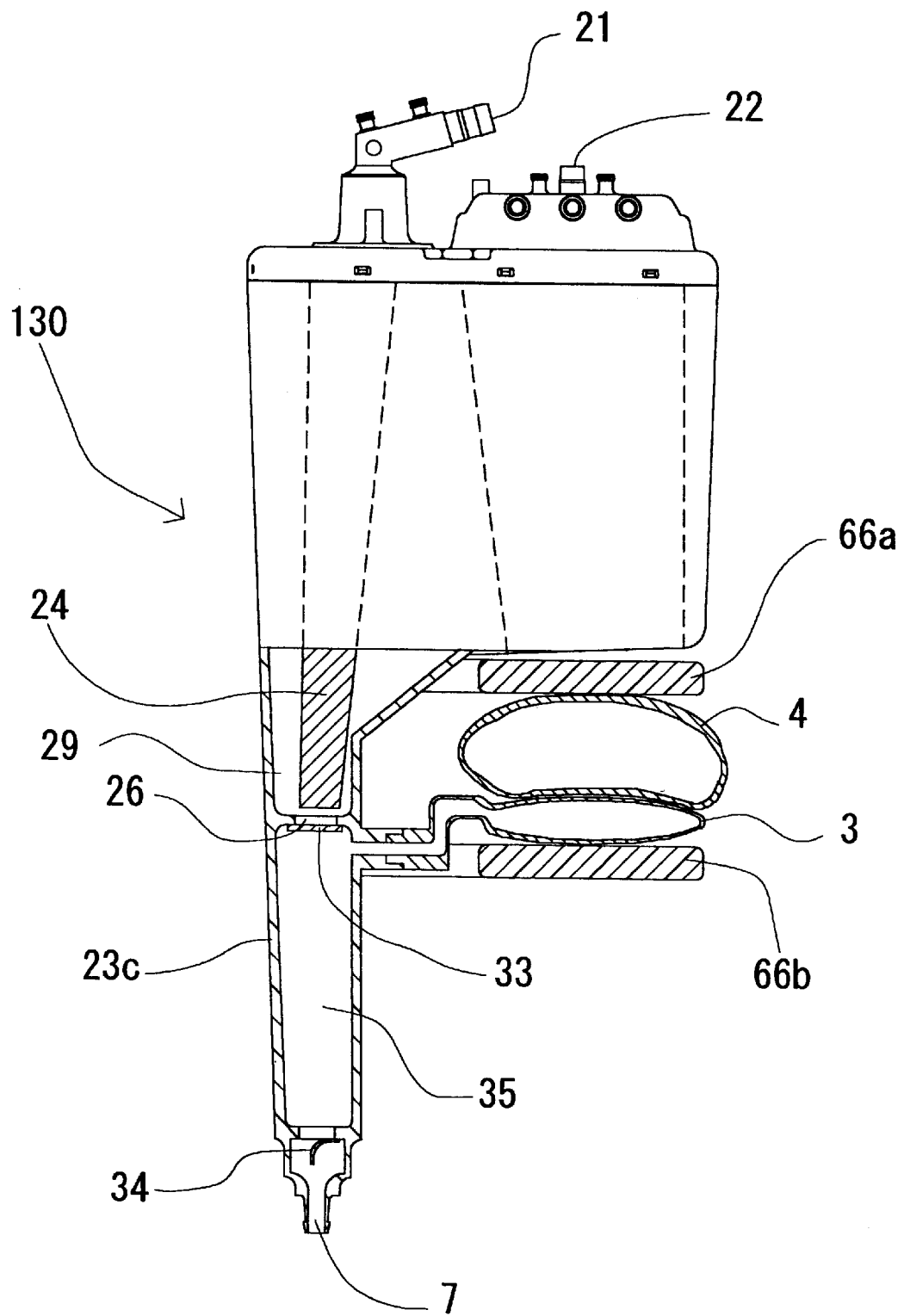

Referring to FIGS. 17 to 23, there is illustrated a blood reservoir 130 according to a further embodiment of the invention. FIG. 17 is a front elevational view of the blood reservoir, FIG. 18 is a left side view of the reservoir, FIG. 19 is a top view of the reservoir, FIG. 20 is a XX—XX cross section of FIG. 17, FIG. 21 is a XXI—XXI cross section of FIG. 18, FIG. 22 is a partial cross-sectional view of FIG. 17, and FIG. 23 is a schematic view for explaining the operation of the blood reservoir of FIG. 17.

The basic construction of the blood reservoir of this embodiment is the same as the reservoir of FIGS. 1 to 9. The difference is the shape and arrangement of a accumulator and blood delivery pumping means and the shape of valves.

As in the first-mentioned embodiment, a blood reservoir 130 includes a blood tank 2 and a blood delivery instrument 6 which includes a blood accumulator 3 and a pumping means 4.

The blood tank 2 includes a tank housing consisting of a main body 23a and a cover 23b both made of rigid resin. The cover 23b is fitted on the top end of housing main body 23a so as to cover the upper opening of the main body 23a as shown in FIGS. 17 and 18. The cover 23b has blood flow inlets 21 and 22 and air vents 27 and 28 as shown in FIG. 19. The blood flow inlet 22 is connected to a cardiotomy line for conveying blood from the operation area. The blood flow inlet 21 is connected to a drainage line for conveying blood from a drainage cannula inserted into the heart ascending/descending veins of the patient. Received in the housing main body 23a are a cardiotomy blood filter 25 for filtering the blood incoming from the inlet 22 and a venous blood filter 24 for filtering the blood incoming from the inlet 21.

The housing main body 23a has a downward projection 23c and a blood outlet 26 (shown in FIG. 21) formed in the bottom of the projection 23c. Defined within the blood tank housing is a blood reserve portion 29 for temporarily reserving blood.

Attached at the bottom of the blood tank 2 is blood delivery instrument 6 which includes a pair of retainer plates 66a and 66b fixedly secured to the tank housing 23a. The blood delivery instrument 6 further includes the blood accumulator 3 and the blood delivery pumping means 4 received between retainer plates 66a and 66b.

A blood channel section 35 is defined by blood delivery instrument 6 near its bottom and provides fluid communication between the blood reserve portion or the interior 29 of the blood tank 2 and the blood accumulator 3. Disposed in proximity to blood flow outlet 26 of blood tank 2 is a first check valve 33 which permits blood passage from the tank 2 to the channel section 35 (and hence, the accumulator 3), but restrains blood passage in the opposite direction. This first check valve 33 functions as a flowpath control member for shutting off communication between the tank 2 and the accumulator 3 during operation of the pumping means 4. The blood deliver instrument 6 is provided with a blood exit port 7 in communication with the blood channel 35. Disposed in proximity to blood exit port 7 is a second check valve 34 which permits blood passage from the channel 35 (and hence, accumulator 3) to a downstream side, but restrains blood passage in the opposite direction. This second check valve 34 functions as a flowpath control member for shutting off blood flow from the downstream side into the accumulator side (and hence, blood channel side) when pumping means 4 is inoperative.

Each check valve 33, 34 has a disc-shaped movable valve body 33a, 34a a part of which is secured to the housing. Preferably the movable valve body is slightly lighter than the specific gravity of blood and a hardness of about 3 to 7 on Shore A scale. For example, the valve body is made of styrene elastomer oil gel or silicone gel and has a thickness of about 1 to 5 mm.

The blood accumulator 3 is in fluid communication with the blood channel section 35 via a blood passage port 31 which is located below or at the lower end of the accumulator 3 and formed at a position of the same height as the lower end of the blood reserve portion 29 of the blood tank 2 in a vertical direction. The blood accumulator 3 includes a tubular portion which extends a certain distance vertically upward and parallel to the projection 23c of the blood tank 2 and bends in a horizontal direction and a bag or bladder portion which is connected to the tubular portion and extends horizontally. The bag portion of the blood accumulator 3 is formed as a bag of flexible resin. When blood flows into the bag portion, it inflates in a height direction of the blood tank 2. If the surface of blood in the blood tank 2 is below the uppermost end of the interior of the blood accumulator 3, an amount proportional to the blood surface in the tank 2 of blood flows into the blood accumulator 3. Inversely, since the maximum containment amount of the blood accumulator 3 remains unchanged, even if the surface of blood in the blood tank 2 is above the uppermost end of the interior of the blood accumulator 3, this maximum containment amount of blood flows into the blood accumulator 3.

Since the uppermost end of the interior of the blood accumulator 3 shown in FIG. 17 is positioned at a lower level than the embodiment shown in FIG. 2, the range (blood surface height range) where the blood accumulator 3 is pressure sensitive (blood surface sensitive) is narrower. In the range where blood accumulator 3 is pressure sensitive, if the volume of blood in the tank 2 is above a predetermined value (that is, the surface of blood in the tank 2 is above the uppermost end of the interior of the accumulator 3 in the illustrated embodiment), the maximum containment amount of the accumulator 3 becomes preferential to the pressure exerted by the volume of blood in the tank 2 so that the accumulator 3 contains the maximum containment amount of blood. If the volume of blood in the tank 2 is below the predetermined value (that is, the surface of blood in the tank 2 is below the uppermost end of the interior of the accumulator 3 in the illustrated embodiment), the accumulator 3 exerts a pressure sensitive function to contain blood in an amount proportional to the volume of blood in the tank 2 (or the height of the blood surface in the tank 2). Thus, the accumulator 3 has the function of automatically containing blood in an amount proportional to the volume of blood in the tank 2 when the volume of blood in the tank 2 is below the predetermined value.

For the accumulator 3 and the pumping means 4, those described in the first-mentioned embodiment are useful It is understood that in accordance with the configuration of the accumulator 3, the pumping means 4 is also configured so as to extend horizontally with respect to the blood tank 2. When an operative fluid is admitted into the pumping means 4, it is inflated to compress accumulator 3 in cooperation with the pair of retainer plates 66a, 66b, thereby displacing blood from the accumulator 3. As seen from FIG. 18, the blood reservoir of this embodiment also has two Frets of accumulators 3 and pumping means 4. The blood channel 35 is also partitioned into two blood channels 35a and 35b which are not in fluid communication with each other, as shown in FIG. 20. Unlike the embodiment shown in FIG. 8, two blood channels 35a and 35b are provided with blood outflow ports 7a and 7b, respectively, as shown in FIG. 18.

Figure 24:
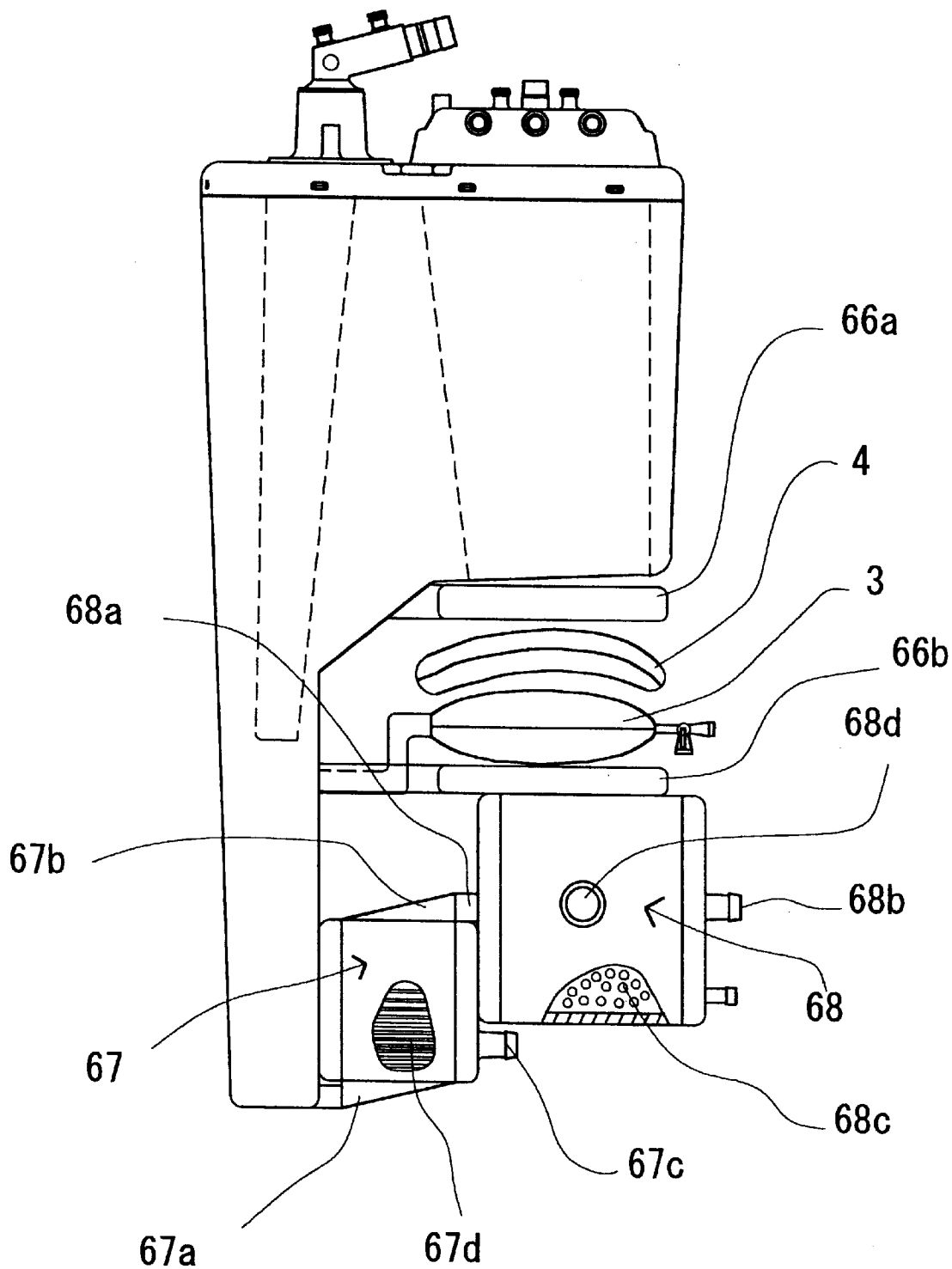
FIG. 24 is a front view of a bloood reservoir having a heat exchanger and an artificial lung integrated therewith.

FIG. 24 shows a blood reservoir having a heat exchanger and an artificial lung integrated therewith The basic construction of this blood reservoir is the same as in FIGS. 17 to 23 except that the blood channel section is vertically elongated and the blood outflow port is horizontally oriented so that a heat exchanger 67 and an artificial lung 68 may be mounted. The description of the basic construction is omitted and only the arrangement of the heat exchanger 67 and the artificial lung 68 is described The artificial lung 68 used herein is a heat exchanger built-in hollow membrane fiber type artificial lung as shown in FIG. 24. The heat exchanger 67 is located upstream and artificial lung 68 is located downstream.

The heat exchanger 67 includes a housing provided with two blood inlet ports 67a (only one shown) connected to two blood outlet ports of the blood reservoir and blood outlet ports 67b as well as an inlet port 67c and an outlet port (not shown) for a heating medium. A multiplicity of heat exchanging tubes 67d are received in the housing and at opposite ends tightly secured to the housing through partitions (not shown). In this heat exchanger, blood passes through the tubes and the heating medium passes outside the tubes. The tubes may be made of metals having high heat conductivity, for example, stainless steel, aluminum and copper or resins. The tubes preferably have an inner diameter of 0.1 to 10 mm, more preferably 0.5 to 5 mm. Usually about 100 to 2,000 tubes are assembled as a bundle which is received within the housing.

The heat exchanger used herein is not limited to the illustrated type wherein blood passes inside the heat exchange tubes (internal blood perfusion type). A heat exchanger of the type wherein blood passes outside the heat exchange tubes (external blood perfusion type) is also useful.

The artificial lung 68 includes a housing having a blood inlet port 68a and a blood outlet port 68b. A bundle consisting of a multiplicity of gas exchanging hollow membrane fibers 68c is received in the housing. The hollow membrane fibers 68c at opposite ends are tightly secured to the housing through partitions (not shown). The housing is provided with a first header opposed to one partition and having a gas inlet port 68d and a second header opposed to the other partition and having a gas outlet port (not shown). The hollow membrane fibers have microscopic pores in the membrane wall through which oxygen is added to blood and carbon dioxide is removed from blood. The hollow membrane fibers used herein generally have a gage of 5 to 80 $\mu$m, preferably 10 to 60 $\mu$m, a porosity of 20 to 80%, preferably 30 to 60%, a pore size of 0.01 to 5 $\mu$m, preferably 0.01 to 1 $\mu$m, and an inner diameter of 100 to 1,000 $\mu$m, preferably 100 to 300 $\mu$m.

Hydrophobic polymers are often used to form the hollow membrane fibers. Exemplary hydrophobic polymers include polypropylene, polyethylene, polytetrafluoroethytene, polysulfone, polyacrylonitrile and cellulose acetate. Preferred among others are polyolefin resins, especially polypropylene. More specifically, hollow membrane fibers of polypropylene in which micropores are formed by a drawing or solid-liquid phase separation method are desirable. Usually 10,000 to 80,000 hollow membrane fibers are distributed over the transverse cross section of the housing.

In this artificial lung, blood passes outside the hollow membrane fibers while gas passed through the hollow membrane fibers. An artificial lung of the type wherein blood passes through the hollow membrane fibers (internal blood perfusion type) is also acceptable. When the blood delivery instrument mentioned above produces a pulsative flow of blood, the use of an artificial lung of the hollow membrane fiber type is preferred because it little absorbs the pulsative flow. The use of an artificial lung comprising porous flat membranes is less desirable because the flat membranes are deformed to a large extent to dampen the pulsation.

The order of a heat exchange and an artificial lung may be reversed if desired.

Figure 26:
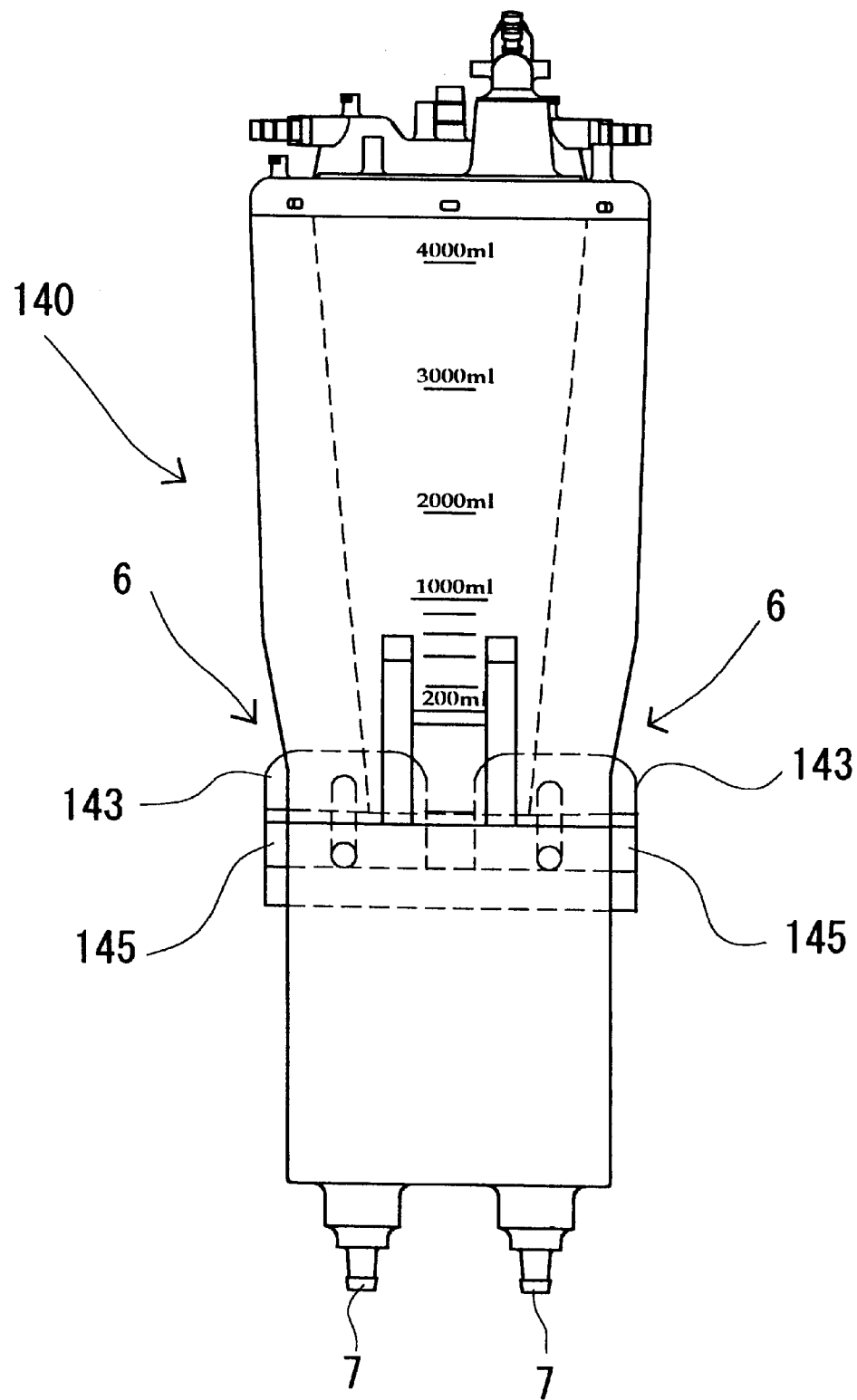
Figure 27:
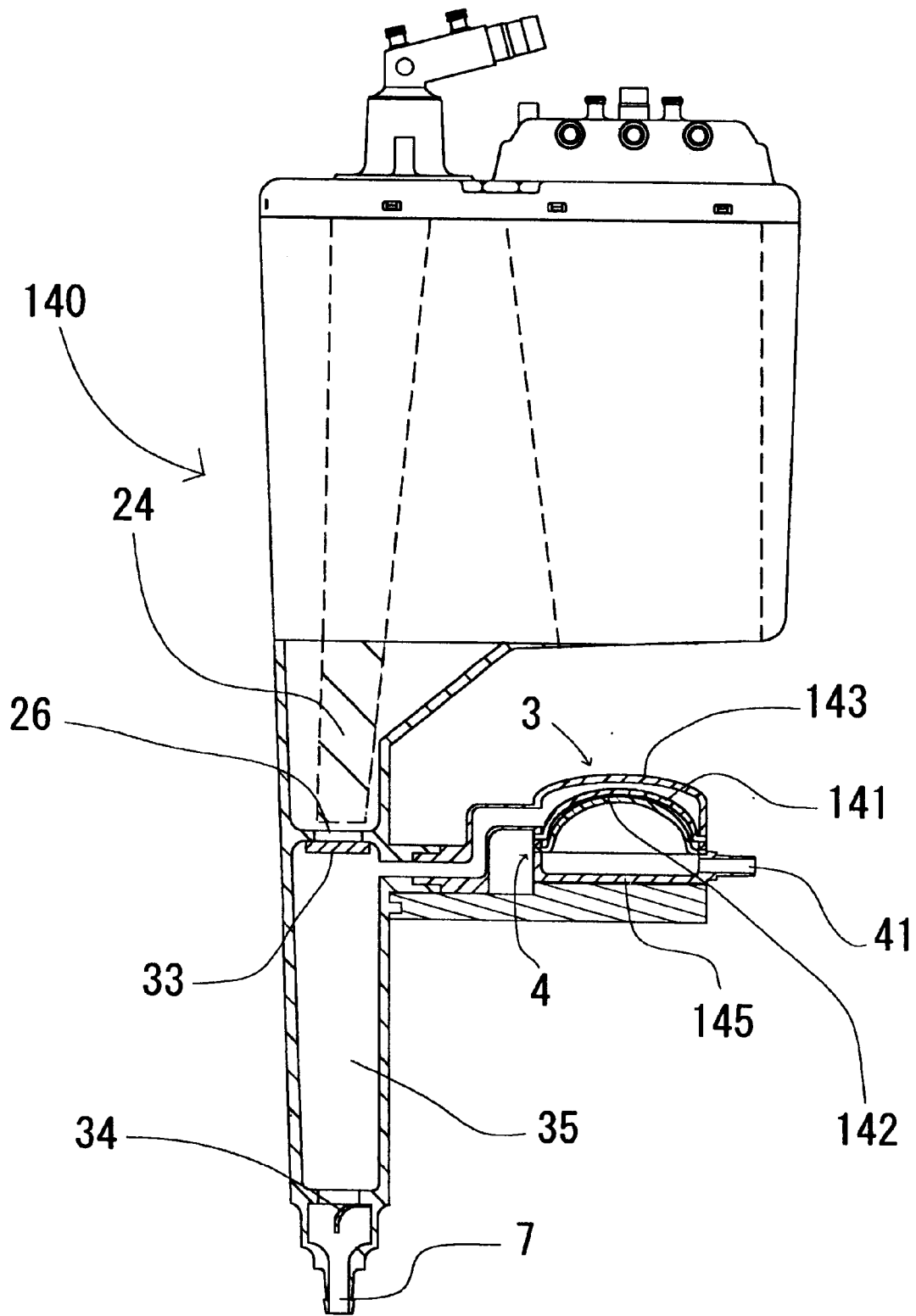

FIGS. 25 to 27 shows a blood reservoir 140 according to a still further embodiment of the invention. FIG. 25 is a front elevation of the blood reservoir; FIG. 26 is a side view of the reservoir; and FIG. 27 is a partial cross-sectional view of the reservoir of FIG. 25. Since the basic construction of this blood reservoir is the same as in FIGS. 17 to 23 except for the blood delivery mechanism, the description of common components is omitted herein.

The blood reservoir 140 of this embodiment includes a blood accumulator side housing 143 of a substantially fixed volume in communication with a blood channel section 35 and a blood accumulator side movable membrane 141 of flexible material disposed below the housing for constructing a blood accumulator 3. Also included are a pumping side housing 145 of a substantially fixed maximum volume in communication with a fluid port 41 and a blood delivery pumping side movable membrane 142 of flexible material disposed above the housing for constructing a blood delivery pumping means 4. The blood accumulator side housing 143 and the pumping side housing 145 are combined and fixedly secured such that the movable membranes associated therewith may face in contact (substantially plane contact), thereby constructing a blood delivery instrument 6. Since the movable membrane 141 on the blood accumulator side and the movable membrane 142 on the pumping means side are separate, the movable membrane on the blood accumulator side is not sucked when a negative pressure is created in the interior of the pumping means upon exhaustion of operative fluid. This prevents the accumulator itself from carrying out blood suction and thus eliminates any influence on the pressure sensitivity of the accumulator. The movable membrane on the accumulator side is one free of self-shape-recovery ability.

Figure 28:
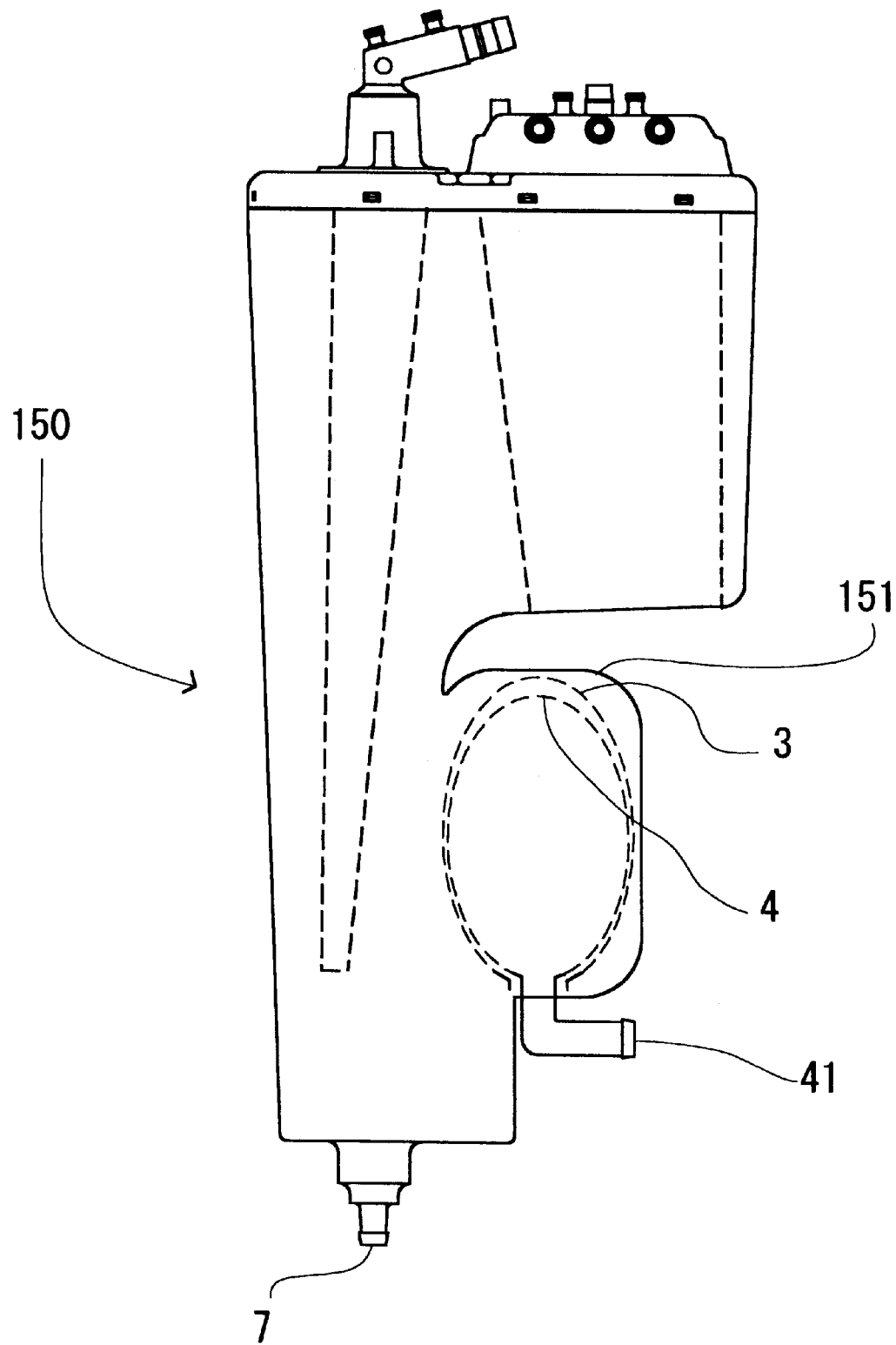
FIGS. 28 to 31 show a blood reservoir according to a still further embodiment of the invention.
Figure 29:
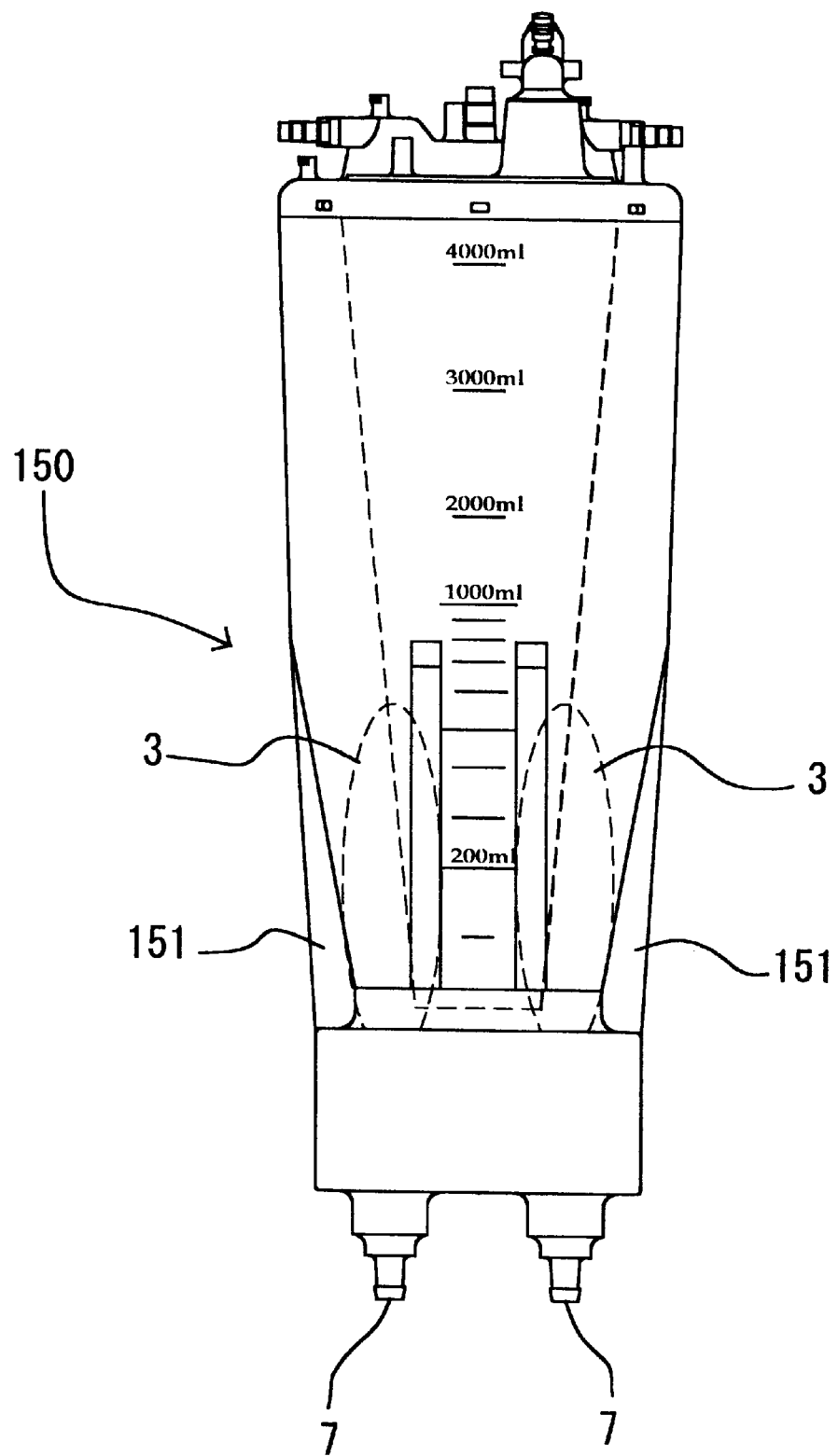
Figure 30:
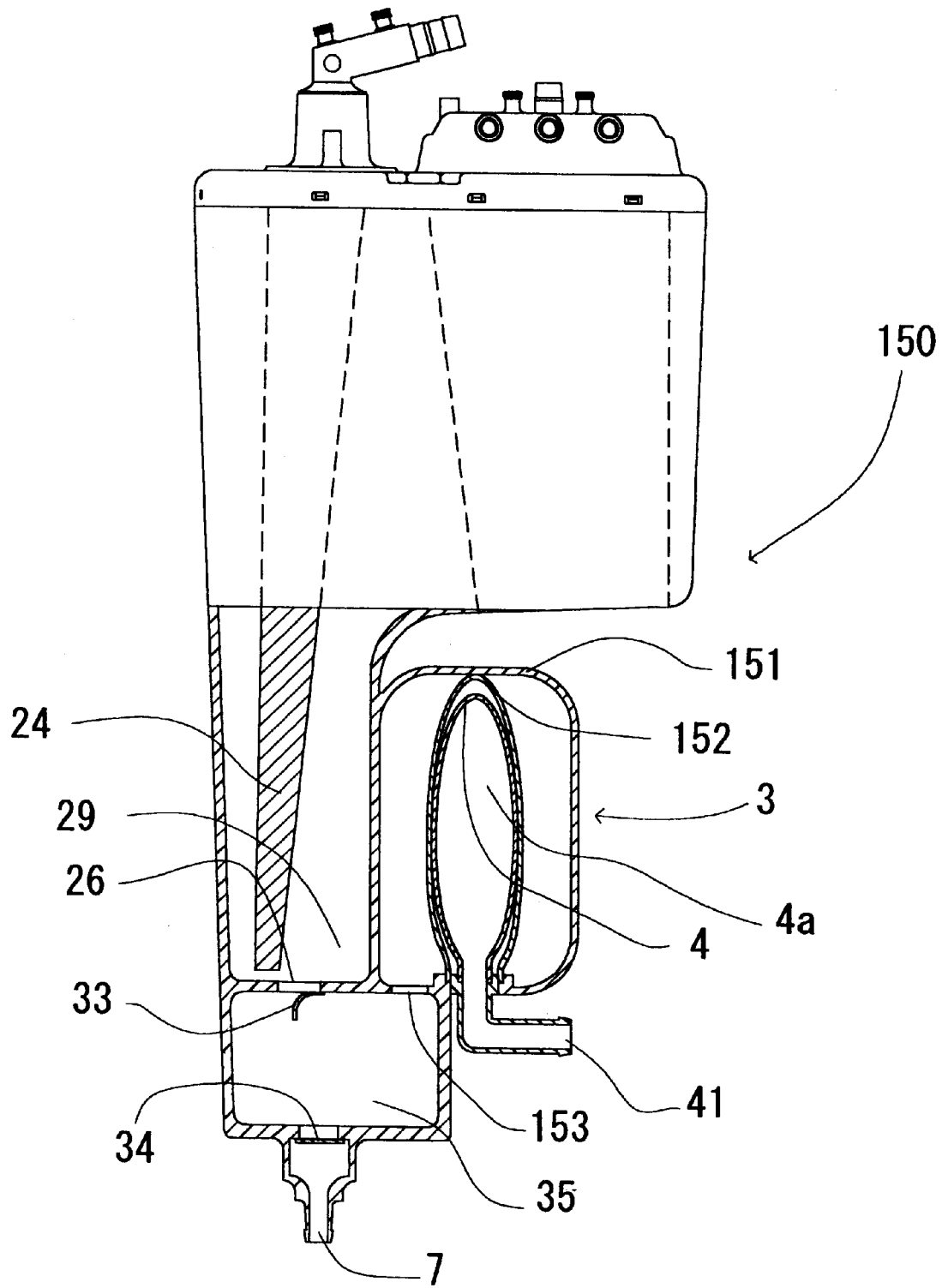
Figure 31:
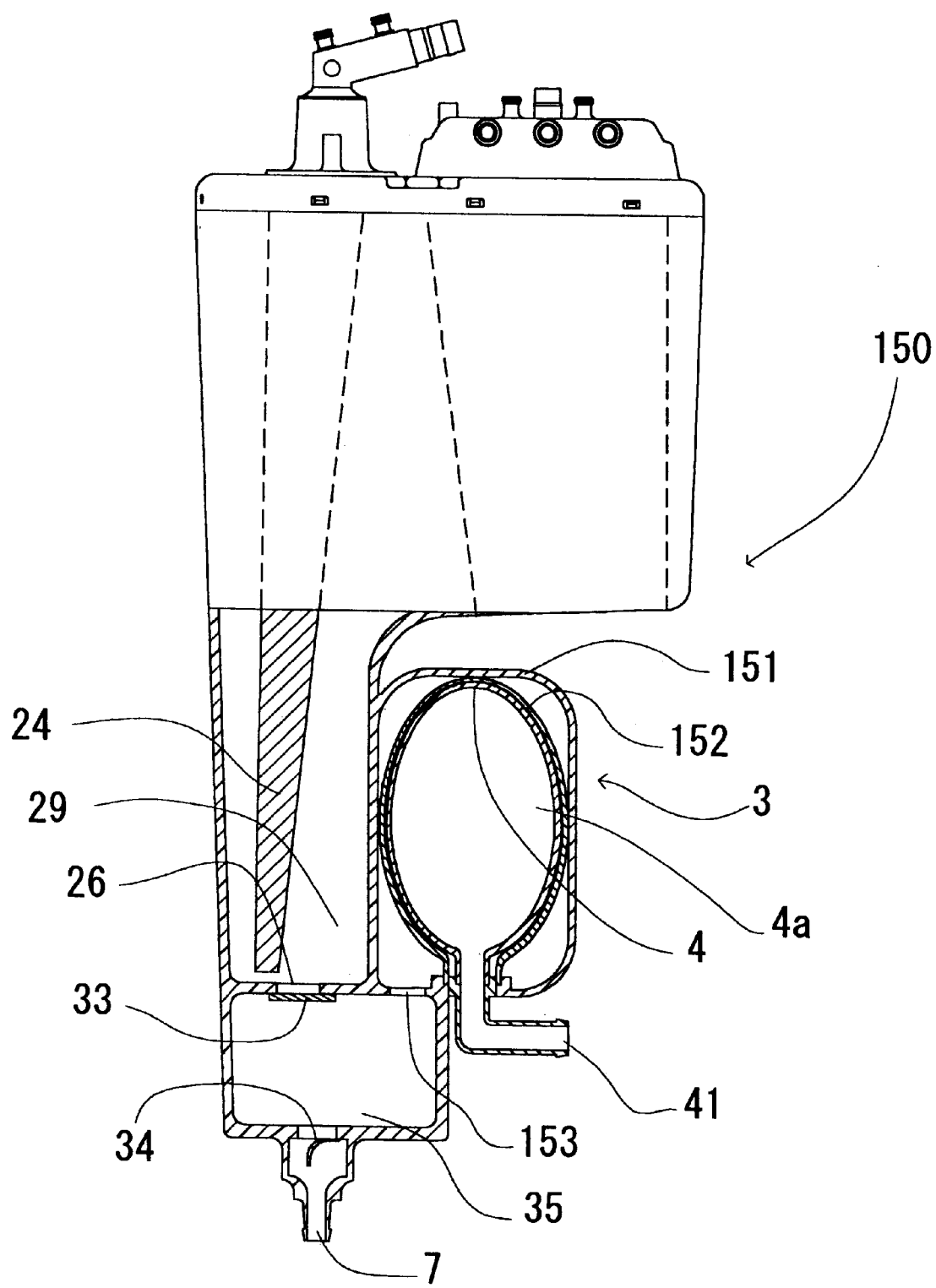

FIGS. 28 to 31 shows a blood reservoir 150 according to a still further embodiment of the invention. FIG. 28 is a front elevation of the blood reservoir; FIG. 29 is a side view of the reservoir; FIG. 30 is a partial cross-sectional view of the reservoir; and FIG. 31 is a schematic view for explaining the operation of the blood reservoir of FIG. 28. Since the basic construction of this blood reservoir is the same as in FIGS. 17 to 23 except for a blood delivery mechanism, the description of common components is omitted herein.

The blood reservoir 150 of this embodiment includes a blood accumulator side housing 151 in communication with a blood channel section 35 by a hole 153 and having a limited maximum volume and a bag-shaped flexible member 152 received in the housing 151 and in communication with the exterior for constructing a blood accumulator 3. Received within the flexible bag is a blood delivery pumping means 4. The blood delivery pumping means 4 used herein is preferably a flexible bag formed of flexible resin as used in the previously mentioned blood accumulator member and defining a space 4a therein. That is, the blood delivery instrument of this blood reservoir 150 has a dual bag structure. The space 4a defined in the blood delivery pumping means 4 is in fluid communication with a fluid passage port 41 disposed at a lower end thereof. On use, the port 41 is connected to a blood delivery fluid feed unit and a compressor built in the fluid feed unit operates to discharge a fluid (either liquid or gas) into and out of the interior space of the pumping bag 4 whereby pumping bag 4 undergoes repetitive inflation and contraction. Upon contraction, the pumping bag 4 is in contact with the accumulator bag 3, but does not force accumulator bag 3 as shown in FIG. 30. Upon inflation, pumping bag 4 inflates to exert an outward pressure against the flexible bag of the accumulator as shown in FIG. 31, reducing the volume of the accumulating bag to displace blood out of the accumulating bag.

Since the deformable portion (flexible bag) of the accumulating member and the deformable portion (flexible bag) of the pumping means are separate in this blood delivery instrument too, the movable membrane on the blood accumulator side is not sucked when a negative pressure is created in the interior of the pumping means upon exhaustion of operative fluid This prevents the blood accumulator itself from carrying out blood suction and thus eliminates any influence on the pressure sensitivity of the blood accumulator. The movable membrane on the blood accumulator side is one free of self-shape-recovery ability.

Figure 15:
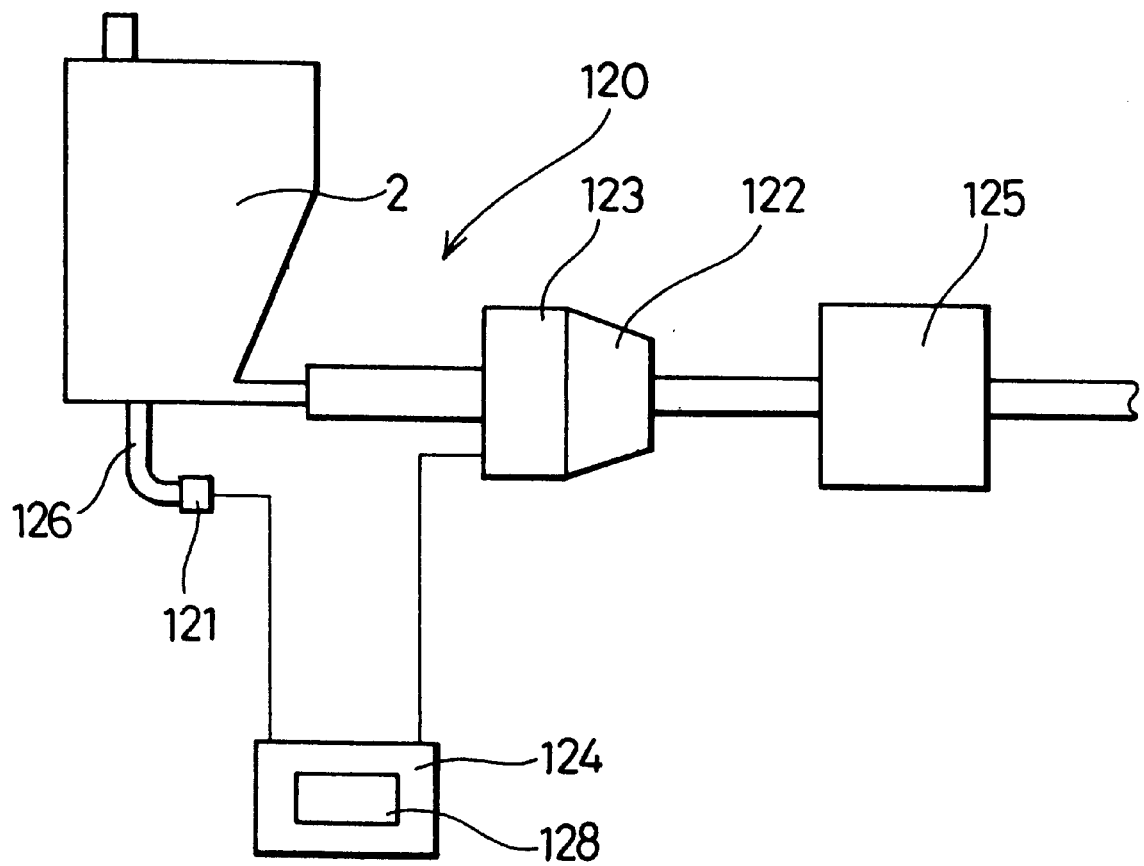
FIG. 15 is a schematic view of a blood delivery apparatus according to a further embodiment of the invention.

Next, the blood delivery apparatus shown in FIG. 15 is described.

The blood delivery apparatus 120 includes a sensor 121 attached to blood tank 2, a blood feed pump 122 connected to the outlet of the tank 2, a motor 123 associated with pump 122 for operating it, and a controller 124 electrically connected to the sensor 121 and the motor 123. The controller 124 has a blood delivery rate regulating function of delivering blood in an amount proportional to the volume of blood reserved in the blood tank 2 when the volume of blood reserved in the blood tank 2 is below a predetermined value.

The sensor 121 is attached to an end of a tube 126 connected to the bottom of the tank 2 so that the sensor is in fluid communication with the tank. A pressure transducer is preferred as the sensor used herein. It is also acceptable to use a load cell to directly measure the weight of the blood bank.

The blood feed pump 122 may he a constant pressure pump, roller pump or peristaltic pump, with the constant pressure pump being preferred. In the illustrated embodiment, a constant pressure pump is used as the blood feed pump. The constant pressure pump includes a centrifugal pump, turbine pump and screw pump.

The sensor 121 detects the pressure at the bottom of the tank 2 and delivers detection signals at suitable time intervals (for example, of about 10 seconds) to the controller 124. It is understood that the pressure at the bottom of the tank 2 is in proportion to the volume of blood reserved in the tank 2. The controller 124 includes a switch panel 128 which includes a flow rate input switch and a switch for inputting a residual blood volume for switching to a flow rate regulating mode. The controller 124 has a residual blood volume computing function of converting a signal from the sensor 121 into a value X corresponding to the residual volume of blood in the blood tank 2. The controller 124 also has a function of comparing a residual blood volume value A (liter) input from the residual blood volume input switch with the actual residual blood volume value X (liter). It maintains the normal blood delivery mode if A ⪇ X, but switches into a blood delivery rate regulating mode to the control feed pump 122 in that mode if A>X. That is, the flow rate of blood to be delivered is regulated after the actual volume X of blood in the blood tank 2 is below the preset residual blood volume value A Specifically, provided that the flow rate input switch inputs a flow rate of B liter/min., the control is made so as to provide a flow rate of blood delivered $Y=B/A \times X$. The invention is not limited to this method of controlling the blood flow rate in a linear proportional manner. For example, control is made such that the blood flow rate changes in a curvilinear proportion as given by $Y=B/A^2 \times X^2$. If A<X is resumed, transition from the blood delivery rate regulating mode to the normal blood delivery mode occurs to resume blood delivery in the preset flow rate C.

There has been described a blood reservoir comprising a blood tank, a blood accumulator connected in fluid communication with an outlet of the tank for receiving blood from the tank, and a pumping means for driving the accumulator to displace blood out of the accumulator for blood delivery purpose. The accumulator is adapted to store blood in an amount proportional to the volume of blood in the tank when the volume of blood in the tank is reduced below a predetermined value. The pumping means operates to intermittently displace blood out of the accumulator. The pumping means is able to regulate the amount of blood displaced out of the accumulator. Therefore, when the volume of blood in the tank is reduced below the predetermined value by an octopus which the blood inflow volume to the tank decreases, the blood is delivered in an amount proportional to the residual blood volume in the tank. In other words, it becomes that the blood delivery volume from the tank is substantially same the blood inflow volume to the tank after the volume of blood in the tank is reduced below the predetermined value.

As the residual blood volume is reduced, the amount of blood delivered is reduced and approaches to zero, but does not equal zero. Blood delivery is maintained even in a very small amount. Since no interruption of blood delivery occurs, no blood stagnation occurs in the extracorporeal blood circulation circuit on a side downstream of the blood reservoir.

Also there has been described a blood reservoir comprising a blood tank, a blood accumulator connected in fluid communication with an outlet of the tank for receiving blood from the tank, a first check valve disposed between the tank and the accumulator for restraining blood passage to the tank side, a second check valve disposed downstream of the accumulator for restraining blood passage from a side downstream of the accumulator, and a pumping means for driving the accumulator for delivering blood out of the accumulator. The accumulator is adapted to store blood in an amount proportional to the volume of blood in the tank when the volume of blood in the tank is reduced below a predetermined value. Since two check valves are included, a satisfactory blood flow can be formed so that the accumulator may exert its function more effectively.

Also there has been described a blood delivery instrument for use in an extracorporeal circulation circuit including a blood tank, comprising a coupling connected to the tank, a blood accumulator connected to the coupling for receiving blood from the tank, and a pumping means for driving the accumulator to deliver blood from the accumulator to a destination. The accumulator is adapted to store blood in an amount proportional to the volume of blood in the tank when the volume of blood in the tank is reduced below a predetermined value. The pumping means operates to intermittently displace blood out of the accumulator Therefore, when the volume of blood in the tank is reduced below the predetermined value by an octopus which the blood inflow volume to the tank decreases, the blood is delivered in an amount proportional to the residual blood volume in the tank. In other words, it becomes that the blood delivery volume from the tank is substantially same the blood inflow volume to the tank after the volume of blood in the tank is reduced below the predetermined value.

As the residual blood volume is reduced, the amount of blood delivered is reduced and approaches to zero, but does not equal zero. Blood delivery is maintained even in a very small amount. Since no interruption of blood delivery occurs, no blood stagnation occurs in the extracorporeal blood circulation circuit on a side downstream of the blood delivery instrument.

Also there has been described a blood delivery instrument for use in an extracorporeal circulation circuit including a blood tank, comprising a coupling connected to the tank, a blood accumulator connected to the coupling for receiving blood from the tank, a first check valve disposed in proximity to the coupling for restraining blood passage from the accumulator to the tank side, a second check valve disposed downstream of the accumulator for restraining blood passage from a side downstream of the accumulator, and a pumping means for driving the accumulator to deliver blood from the accumulator to a destination. The accumulator is adapted to store blood in an amount proportional to the volume of blood in the tank when the volume of blood in the tank is reduced below a predetermined value since two check valves are included, a satisfactory blood flow can be formed so that the accumulator may exert its function more effectively.

Also there has been described a blood delivery apparatus for use in an extracorporeal circulation circuit including a blood tank, comprising a blood delivery amount regulating means for regulating the amount of blood delivered so as to be in proportion to the volume of blood in the tank when the volume of blood in the tank is reduced below a predetermined value. Therefore, when the volume of blood in the tank is reduced below the predetermined value by an octopus which the blood inflow volume to the tank decreases, the blood is delivered in an amount proportional to the residual blood volume in the tank. In other words, it becomes that the blood delivery volume from the tank is substantially same the blood inflow volume to the tank after the volume of blood in the tank is reduced below the predetermined value. As the residual blood volume is reduced, the amount of blood delivered is reduced and approaches to zero, but does not equal zero. Blood delivery is maintained even in a very small amount. Since no interruption of blood delivery occurs, no blood stagnation occurs in the extracorporeal blood circulation circuit on a side downstream of the blood delivery apparatus.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A blood reservoir comprising
   a blood tank having a blood outlet and
   a blood accumulator connected in fluid communication with the tank outlet for receiving blood from said tank and adapted to store blood in an amount proportional to the volume of blood in said tank when the volume of blood in said tank is reduced below a predetermined value,
   pumping means adapted to be intermittently operated for driving said accumulator to displace blood out of said accumulator for blood delivery purpose, said pumping means being able to regulate the amount of blood displaced out of said accumulator, the amount of blood stored in said blood accumulator being independent of operation of said pumping means.

2. The blood reservoir of claim 1 wherein said accumulator includes a deformable portion formed of flexible material and said pumping means operates to press said accumulator to deform the deformable portion thereof to displace blood out of said accumulator upon blood delivery.

3. The blood reservoir of claim 1 wherein said blood tank is vertically oriented and has a blood reserve portion and a outlet located at a lower end portion thereof, and said accumulator is located upwards of said outlet.

4. The blood reservoir of claim 1 wherein said accumulator is adapted to store a predetermined amount of blood when the volume of blood in said tank is above the predetermined value, but store blood in a varying amount proportional to the volume of blood in said tank when the volume of blood in said tank is reduced below the predetermined value.

5. The blood reservoir of claim 1 wherein said accumulator comprises a flexible accumulating member and said pumping means comprises a flexible container adapted to be charged with and emptied of fluid and to contact the flexible accumulating member, wherein when fluid is admitted into said flexible container, the flexible container is inflated to press the flexible accumulating member for displacing blood out of said accumulating member.

6. The blood reservoir claim 1 further comprising a housing associated with said tank and a movable membrane of flexible material disposed in said housing for defining first and second chambers, the first chamber constructing said accumulator and the second chamber constructing said pumping means.

7. The blood reservoir of claim 1 further comprising a blood delivery fluid feed machine coupled to said pumping means for moving a fluid into and out of said pumping means for operating said pumping means.

8. The blood reservoir of claim 1 wherein at least two accumulators are provided.

9. The blood reservoir of claim 1 wherein at least two sets of accumulators and pumping means are provided.

10. The blood reservoir of claim 1 wherein at least two sets of accumulators and pumping means are provided, said reservoir further comprising a blood delivery fluid feed machine coupled to the respective pumping means for moving a fluid into and out of the respective pumping means, said fluid feed machine including means for controlling the timing of delivering blood out of said accumulators.

11. The blood reservoir of claim 1 wherein said pumping means is removable from said blood reservoir.

12. A blood reservoir comprising
    a blood tank having a blood outlet,
    a blood accumulator connected in fluid communication with the tank outlet for receiving blood from said tank and adapted to store blood in an amount proportional to the volume of blood in said tank when the volume of blood in said tank is reduced below a predetermined value,
    a first check valve disposed between said tank and said accumulator for restraining blood passage to the tank side,
    a second check valve disposed downstream of said accumulator for restraining blood passage from a side downstream of said accumulator, and
    pumping means for driving said accumulator for delivering blood out of said accumulator, the amount of blood stored in said blood accumulator being independent of operation of said pumping means.

13. The blood reservoir of claim 12 further comprising a containment having said accumulator received therein, said containment being provided with a port to be coupled to hydraulic means for pressurizing the interior of said containment.

14. The blood reservoir of claim 12 wherein said accumulator includes a deformable portion formed of flexible material and said pumping means operates to press said accumulator to deform the deformable portion thereof to displace blood out of said accumulator upon blood delivery.

15. The blood reservoir of claim 12 wherein said blood tank is vertically oriented and has a blood reserve portion and a outlet located at a lower end portion thereof, and said accumulator is located upwards of said outlet.

16. The blood reservoir of claim 12 wherein said accumulator is adapted to store a predetermined amount of blood when the volume of blood in said tank is above the predetermined value, but store blood in a varying amount proportional to the volume of blood in said tank when the volume of blood in said tank is reduced below the predetermined value.

17. The blood reservoir of claim 12 wherein said accumulator comprises a flexible accumulating member and said pumping means comprises a flexible container which will come in contact with the flexible accumulating member and which can be charged with or emptied of a fluid, wherein when the fluid is admitted into said flexible container, the flexible container is inflated to press the flexible accumulating member for displacing blood out of said accumulating member.

18. The blood reservoir of claim 12 further comprising a blood delivery fluid feed machine coupled to said pumping means for moving a fluid into and out of said pumping means for operating said pumping means.

19. The blood reservoir of claim 12 wherein at least two sets of accumulators and pumping means are provided, said reservoir further comprising a blood delivery fluid feed machine coupled to the respective pumping means for moving a fluid into and out of the respective pumping means, said fluid feed machine including means for controlling the timing of delivering blood out of said accumulators.

20. The blood reservoir of claim 12 wherein said pumping means is removable from said blood reservoir.

21. A blood reservoir comprising
a blood tank having a blood outlet,
a blood accumulator connected in fluid communication with the tank outlet for receiving blood from said tank and adapted to store blood in an amount proportional to the volume of blood in said tank when the volume of blood in said tank is reduced below a predetermined value, and
a containment having said accumulator received therein, said containment being provided with a port to be coupled to hydraulic or pneumatic means for pressurizing the interior of said containment, the amount of blood stored in said blood accumulator being independent of pressurization of said interior of said containment.

22. The blood reservoir of claim 21 further comprising a first check valve disposed between said tank and said accumulator for restraining blood passage to the tank side and a second check valve disposed downstream of said accumulator for restraining blood passage from a side downstream of said accumulator.

23. The blood reservoir of claim 21 wherein said blood tank is vertically oriented and has a blood reserve portion and a outlet located at a lower end portion thereof, and said accumulator is located upwards of said outlet.

24. The blood reservoir of claim 21 wherein said accumulator is adapted to store a predetermined amount of blood when the volume of blood in said tank is above the predetermined value, but store blood in a varying amount proportional to the volume of blood in said tank when the volume of blood in said tank is reduced below the predetermined value.

25. The blood reservoir of claim 21 wherein at least two sets of accumulators and containments are provided, said reservoir further comprising a blood delivery fluid feed machine coupled to the respective containment for moving a fluid into and out of the respective containment, said fluid feed machine including means for controlling the timing of delivering blood out of said accumulators.

26. A blood delivery instrument for use in an extracorporeal blood circulation circuit including a blood tank, comprising
a coupling connected to said tank,
a blood accumulator connected to said coupling for receiving blood from said tank and adapted to store blood in an amount proportional to the volume of blood in said tank when the volume of blood in said tank is reduced below a predetermined value,
pumping means adapted to be intermittently operated for driving said accumulator to deliver blood from said accumulator to a destination, the amount of blood stored in said blood accumulator being independent of operation of said pumping means,
a first check valve disposed between said tank and said accumulator for restraining blood passage to the tank side, and
a second check valve disposed downstream of said accumulator for restraining blood passage from a side downstream of said accumulator.

27. The blood delivery instrument of claim 26 wherein said accumulator comprises an accumulating bag of flexible material which is adapted to store a predetermined a mount of blood when the volume of blood in said tank is above the predetermined value, but store blood in a varying amount proportional to the volume of blood in said tank when the volume of blood in said tank is reduced below the predetermined value.

28. The blood delivery instrument of claim 26 wherein said accumulator comprises a flexible accumulating member and said pumping means comprises a flexible container which will come in contact with the flexible accumulating member and which can be charged with or emptied of a fluid, wherein when the fluid is admitted into said flexible container, the flexible container is inflated to press the flexible accumulating member for displacing blood out of said accumulating member.

29. The blood delivery instrument of claim 26 further comprising a blood delivery fluid feed machine coupled to said pumping means for moving a fluid into and out of said pumping means for operating said pumping means.

* * * * *

UNITED STATES PATENT AND TRADEMARK OFFICE
CERTIFICATE OF CORRECTION

PATENT NO. : 5,931,646
DATED : August 3, 1999
INVENTOR(S) : NOGAWA, et al.

It is certified that error appears in the above-indentified patent and that said Letters Patent is hereby corrected as shown below:

At Column 4, line 42, delete "four" and insert --for--.
At Column 8, line 10, delete "methylenle" and insert --methylene--.
At Column 8, line 14, delete "disocyanate" and insert --diisocyanate--.
At Column 12, line 1, delete "the".
At Column 14, line 51, delete "FIG. 18" and insert --FIG. 17--.
At Column 16, line 39, delete "Frets" and insert --sets--.
At Column 18, line 2, delete "145" and insert --143--.
At Column 21, line 1, delete "value since" and insert --value. Since--
In Claim 27, line 3, delete "a mount" and insert --amount--.

Signed and Sealed this

Eighth Day of February, 2000

Attest:

Q. TODD DICKINSON

*Attesting Officer*  *Commissioner of Patents and Trademarks*